(12) United States Patent (10) Patent No.: US 8,034,819 B2
Fukuda et al. (45) Date of Patent: Oct. 11, 2011

(54) GLUCOKINASE ACTIVATOR

(75) Inventors: Yasumichi Fukuda, Tochigi (JP);
Yoshikazu Asahina, Tochigi (JP);
Masanori Takadoi, Tochigi (JP); Kohei Ohata, Tochigi (JP); Tomohiro Ide, Tochigi (JP); Fumiyoshi Kobayashi, Tochigi (JP); Shinji Kobayashi, Tokyo (JP); Kanji Komatsu, Tokyo (JP); Masanori Yamamoto, Tokyo (JP)

(73) Assignees: Kyorin Pharmaceutical Co., Ltd., Tokyo (JP); Teijin Pharma Limited, Tokyo (JP)

( * ) Notice: Subject to any disclaimer, the term of this patent is extended or adjusted under 35 U.S.C. 154(b) by 0 days.

(21) Appl. No.: 12/449,973

(22) PCT Filed: Mar. 6, 2008

(86) PCT No.: PCT/JP2008/054014
§ 371 (c)(1),
(2), (4) Date: Dec. 18, 2009

(87) PCT Pub. No.: WO2008/111473
PCT Pub. Date: Sep. 18, 2008

(65) Prior Publication Data
US 2010/0099671 A1 Apr. 22, 2010

(30) Foreign Application Priority Data

Mar. 7, 2007 (JP) ................................. 2007-057427
Dec. 27, 2007 (JP) ................................. 2007-336466

(51) Int. Cl.
*A61K 31/4965* (2006.01)
*A61K 31/44* (2006.01)
*A61K 31/426* (2006.01)
*C07D 241/20* (2006.01)
*C07D 213/61* (2006.01)
*C07D 277/38* (2006.01)

(52) U.S. Cl. .................. 514/255.06; 514/352; 514/371; 544/336; 546/309; 548/195

(58) Field of Classification Search .............. 514/233.8, 514/371, 255.06, 407, 352; 544/336, 135; 546/312; 548/195, 372.5
See application file for complete search history.

(56) References Cited

U.S. PATENT DOCUMENTS

| | | | |
|---|---|---|---|
| 6,353,111 B1 | 3/2002 | Corbett et al. | |
| 6,369,232 B1 | 4/2002 | Sidduri | |
| 6,384,220 B2 | 5/2002 | Corbett et al. | |
| 6,388,071 B2 | 5/2002 | Mahaney | |
| 6,388,088 B1 | 5/2002 | Sidduri | |
| 6,433,188 B1 | 8/2002 | Corbett et al. | |
| 6,441,180 B1 | 8/2002 | Sidduri | |
| 6,441,184 B1 | 8/2002 | Corbett et al. | |
| 6,448,399 B1 | 9/2002 | Corbett et al. | |
| 6,482,951 B2 | 11/2002 | Guertin | |
| 6,486,184 B2 | 11/2002 | Kester et al. | |
| 6,489,485 B2 | 12/2002 | Bizzarro et al. | |
| 6,528,543 B1 | 3/2003 | Bizzarro et al. | |
| 6,545,155 B2 | 4/2003 | Corbett et al. | |
| 6,583,288 B2 | 6/2003 | Goodnow, Jr. et al. | |
| 6,608,218 B2 | 8/2003 | Kester et al. | |
| 6,784,298 B2 | 8/2004 | Goodnow, Jr. et al. | |
| 6,911,545 B2 | 6/2005 | Corbett et al. | |
| 7,105,671 B2 | 9/2006 | Corbett et al. | |
| 7,262,196 B2 | 8/2007 | Fyfe et al. | |
| 2001/0051731 A1 | 12/2001 | Bizzarro et al. | |
| 2001/0053851 A1 | 12/2001 | Mahaney | |
| 2001/0056191 A1 | 12/2001 | Goodnow, Jr. et al. | |
| 2002/0002190 A1 | 1/2002 | Corbett et al. | |
| 2002/0035266 A1 | 3/2002 | Sidduri | |

(Continued)

FOREIGN PATENT DOCUMENTS

EP 1 921 074 5/2008

(Continued)

OTHER PUBLICATIONS

International Search Report issued Jun. 10, 2008 in International (PCT) Application No. PCT/JP2008/054014, filed Mar. 6, 2008.
International Preliminary Report on Patentability together with English translation of PCT Written Opinion in PCT application corresponding to present U.S. application, Jun. 2008.
Matschinsky, Franz M., "A Lesson in Metabolic Regulation Inspired by the Glucokinase Glucose Sensor Paradigm", Diabetes, vol. 45, 1996, pp. 223-241.
Liang et al., "Concordant Glucose Induction of Glucokinase, Glucose Usage, and Glucose-Stimulated Insulin Release in Pancreatic Islets Maintained in Organ Culture", Diabetes, vol. 41, 1992, pp. 792-806.
Ferre et al., "Evidence from Transgenic Mice that Glucokinase is Rate Limiting for Glucose Utilization in the Liver", FASEB J., vol. 10, 1996, pp. 1213-1218.
U.S. Appl. No. 12/989,838, filed Nov. 24, 2010 (not yet published).

*Primary Examiner* — Kamal Saeed
*Assistant Examiner* — Kristin Bianchi
(74) *Attorney, Agent, or Firm* — Wenderoth, Lind & Ponack, L.L.P.

(57) ABSTRACT

A compound, or a pharmaceutically acceptable salt thereof, represented by the formula (1),

[Chemical formula 1]

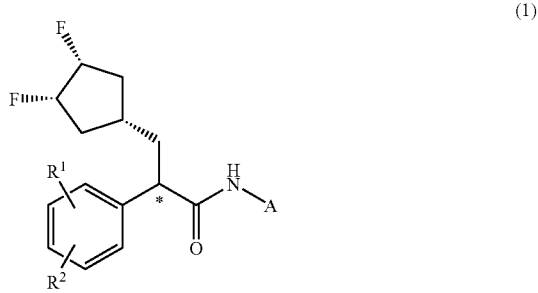

(1)

(wherein, the carbon atom marked with an * is in the R-configuration, $R^1$ represents a hydrogen atom, a halogen atom, an amino group, a hydroxyl group, a hydroxyamino group, a nitro group, a cyano group, a sulfamoyl group, a $C_1$-$C_6$ alkyl group, or a $C_1$-$C_6$ alkoxy group, $R^2$ represents a $C_3$-$C_6$ cycloalkylsulfanyl group, a $C_3$-$C_6$ cycloalkylsulfinyl group, or a $C_3$-$C_6$ cycloalkylsulfonyl group, and A represents a substituted or unsubstituted heteroaryl group).

26 Claims, No Drawings

U.S. PATENT DOCUMENTS

| | | | |
|---|---|---|---|
| 2002/0035267 A1 | 3/2002 | Sidduri | |
| 2002/0042512 A1 | 4/2002 | Kester et al. | |
| 2002/0065275 A1 | 5/2002 | Sidduri | |
| 2002/0082260 A1 | 6/2002 | Guertin | |
| 2002/0103199 A1 | 8/2002 | Corbett et al. | |
| 2002/0103241 A1 | 8/2002 | Corbett et al. | |
| 2002/0107396 A1 | 8/2002 | Corbett et al. | |
| 2002/0111372 A1 | 8/2002 | Corbett et al. | |
| 2002/0198200 A1 | 12/2002 | Kester et al. | |
| 2003/0060625 A1 | 3/2003 | Bizzarro et al. | |
| 2003/0225283 A1 | 12/2003 | Corbett et al. | |
| 2003/0225286 A1 | 12/2003 | Goodnow, Jr. et al. | |
| 2003/0235551 A1 | 12/2003 | Pagilagan | |
| 2004/0147748 A1 | 7/2004 | Chen et al. | |
| 2004/0181067 A1 | 9/2004 | Fyfe et al. | |
| 2004/0186290 A1 | 9/2004 | Fyfe et al. | |
| 2005/0282851 A1 | 12/2005 | Bebernitz | |
| 2006/0141599 A1 | 6/2006 | Corbett et al. | |
| 2006/0178429 A1 | 8/2006 | Corbett et al. | |
| 2007/0129554 A1 | 6/2007 | Harrington et al. | |
| 2007/0265297 A1 | 11/2007 | Bebernitz et al. | |
| 2008/0009465 A1 | 1/2008 | Ryono et al. | |
| 2008/0015358 A1 | 1/2008 | Fyfe et al. | |
| 2008/0021032 A1 | 1/2008 | Berthel et al. | |
| 2008/0021052 A1 | 1/2008 | Chen et al. | |
| 2008/0103167 A1 | 5/2008 | Bebernitz et al. | |
| 2008/0139562 A1 | 6/2008 | Jeppesen et al. | |
| 2008/0242869 A1 | 10/2008 | Fyfe | |
| 2008/0293730 A1 | 11/2008 | Fyfe et al. | |
| 2008/0293741 A1 | 11/2008 | Fyfe et al. | |
| 2008/0312256 A1 | 12/2008 | Bebernitz et al. | |
| 2008/0318948 A1 | 12/2008 | Bebernitz | |
| 2009/0005391 A1 | 1/2009 | Fyfe et al. | |
| 2009/0054444 A1 | 2/2009 | Fyfe et al. | |
| 2010/0016304 A1 | 1/2010 | Fukuda et al. | |

FOREIGN PATENT DOCUMENTS

| | | |
|---|---|---|
| WO | 2004/063194 | 7/2004 |
| WO | 2004/072066 | 8/2004 |
| WO | 2005/103021 | 11/2005 |
| WO | 2006/016174 | 2/2006 |
| WO | 2006/016178 | 2/2006 |
| WO | 2006/016194 | 2/2006 |
| WO | 2006/059163 | 6/2006 |
| WO | 2008/012227 | 1/2008 |

GLUCOKINASE ACTIVATOR

TECHNICAL FIELD

The present invention relates to activators of glucokinase (which may be referred to simply as "GK," hereinafter). Furthermore, the present invention relates to a pharmaceutical composition for the treatment or prevention of diabetes, obesity and the like and having a GK activator as an active ingredient.

BACKGROUND ART

According to a patient survey carried out by the Ministry of Health, Labour and Welfare of Japan in 2002, the total number of Japanese diabetes patients is 2.28 million. According to a diabetes fact-finding survey carried out in the same year, the combined total of "people strongly suspected of having diabetes" and "people for whom the possibility of diabetes cannot be denied" has increased to 16.20 million, meaning that diabetes is a problem.

Japanese people have a genetic factor for a weak insulin secretory capacity, and thus the Japanese domestic market is centered on insulin hyposecretion. However, due to the trend toward a more Western diet, recent years have seen a gradual increase in the number of patents with insulin resistance. Therefore, there is a need for drugs which can be expected to be effective against both insulin hyposecretion and insulin resistance.

Glucokinase (GK), which catalyzes the phosphorylation of glucose, functions as a glucose sensor in the body, and increases the secretion of insulin and the utilization of glucose in the liver during periods of high glucose levels. Diabetic patients are unable to normally maintain glucose homeostatis in their bodies. Thus, by activating GK, insulin secretion in the pancreas, which is glucose concentration dependent, is promoted. This has a dual action of increasing the utilization of glucose in the liver and suppressing the release of glucose. As a result, blood glucose decreases (Non-Patent Documents 1 to 3). Therefore, it is desirable to provide a GK activator which exhibits an effect as a diabetes drug on both insulin hyposecretion (pancreatic effect) and insulin resistance (hepatic effect).

Examples of known GK activators include various amide compounds (Patent Documents 11 to 19) such as arylcycloalkylpropionamides (Patent Document 1), 2,3-disubstituted transolefinic N-heteroaromatic ring—or ureidopropionic amides (Patent Document 2), alkynylphenyl heteroaromatic amides (Patent Document 3), hydantoins (Patent Document 4), substituted phenylacetamides (Patent Document 5), para-alkyl, allyl, cycloheteroalkyl or heteroaryl (carbonyl or sulfonyl) amine substituted phenylamides (Patent Document 6), alpha-acyl and alpha-heteroatom substituted benzene acetamides (Patent Document 7), tetrazolylphenylacetamides (Patent Document 8), fused heteroaromatic compound (Patent Document 9), and phenylacetamides having a cycloalkane with a single carbon atom substituted or heterocyclic ring (Patent Document 10). However, there has been no disclosure of GK activators in which two fluorine atoms are substituted on different carbon atoms of a cyclopentyl group.

[Patent Document 1] WO2000/058293 Pamphlet
[Patent Document 2] WO2001/044216 Pamphlet
[Patent Document 3] WO2001/083465 Pamphlet
[Patent Document 4] WO2001/083478 Pamphlet
[Patent Document 5] WO2001/085706 Pamphlet
[Patent Document 6] WO2001/085707 Pamphlet
[Patent Document 7] WO2002/008209 Pamphlet
[Patent Document 8] WO2002/014312 Pamphlet
[Patent Document 9] WO2002/046173 Pamphlet
[Patent Document 10] WO2003/095438 Pamphlet
[Patent Document 11] WO2004/052869 Pamphlet
[Patent Document 12] WO2004/072031 Pamphlet
[Patent Document 13] WO2004/072066 Pamphlet
[Patent Document 14] WO2005/103021 Pamphlet
[Patent Document 15] WO2006/016174 Pamphlet
[Patent Document 16] WO2006/016178 Pamphlet
[Patent Document 17] WO2006/016194 Pamphlet
[Patent Document 18] WO2006/059163 Pamphlet
[Patent Document 19] U.S. Pat. No. 6,911,545
[Non-Patent Document 1] Diabetes 45, 223-241 (1996)
[Non-Patent Document 2] Diabetes 41, 792-806 (1992)
[Non-Patent Document 3] FASEB J. 10, 1213-1218 (1996)

DISCLOSURE OF THE INVENTION

Problems to be Solved by the Invention

It is an object of the present invention to provide a compound having an excellent GK-activating effect or hypoglycemic effect, which is useful in the treatment or prevention of diabetes, obesity and the like.

Means for Solving the Problems

As a result of extensive studies to resolve the above problems, the present inventors discovered that, among propionamide compounds having 3,4-difluorocyclopentyl group at the 3-position thereof, those having a specific stereostructure exhibit an excellent GK-activating effect and hypoglycemic effect, thereby completing the present invention.

Specifically, the present invention relates to:

1) A compound represented by the general formula (1), or a pharmaceutically acceptable salt thereof:

[Chemical formula 1]

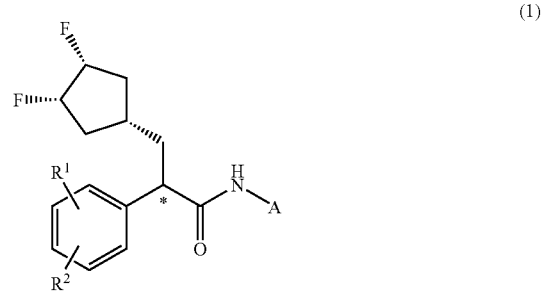

(wherein, the carbon atom marked with an * is in the R-configuration, $R^1$ represents a hydrogen atom, a halogen atom, an amino group, a hydroxyl group, a hydroxyamino group, a nitro group, a cyano group, a sulfamoyl group, a $C_1$-$C_6$ alkyl group, or a $C_1$-$C_6$ alkoxy group, $R^2$ represents a $C_3$-$C_6$ cycloalkylsulfanyl group, a $C_3$-$C_6$ cycloalkylsulfinyl group, or a $C_3$-$C_6$ cycloalkylsulfonyl group, and A represents a substituted or unsubstituted heteroaryl group);

2) The compound according to 1), or a pharmaceutically acceptable salt thereof, wherein $R^1$ is a hydrogen atom and $R^2$ is a $C_3$-$C_6$ cycloalkylsulfonyl group;

3) The compound according to 1), or a pharmaceutically acceptable salt thereof, wherein $R^1$ is a hydrogen atom and $R^2$ is a cyclopropylsulfonyl group;

4) The compound according to any of 1) to 3), represented by the general formula (1a), or a pharmaceutically acceptable salt thereof:

[Chemical formula 2]

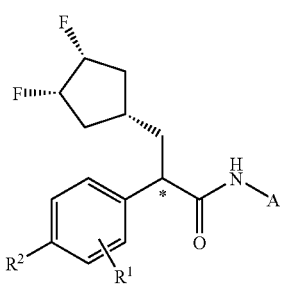

(1a)

(wherein the *, $R^1$, $R^2$, and A are as defined above);

5) The compound according to any of 1) to 3) represented by the general formula (1b), or a pharmaceutically acceptable salt thereof:

[Chemical formula 3]

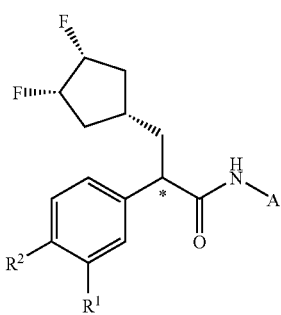

(1b)

(wherein the *, $R^1$, $R^2$, and A are as defined above);

6) The compound according to any of 1) to 5), or a pharmaceutically acceptable salt thereof, wherein A is a heteroaryl group that is unsubstituted or monosubstituted with a halogen atom, a $C_1$-$C_6$ alkyl group, a $C_1$-$C_6$ alkoxy group, a nitro group, a cyano group, or a group represented by the formula, —$(CH_2)_m C(O)OR^3$ (wherein $R^3$ represents a hydrogen atom or a $C_1$-$C_6$ alkyl group and m is an integer of 0 to 2);

7) The compound according to any of 1) to 5), or a pharmaceutically acceptable salt thereof, wherein A is a heteroaryl group unsubstituted or monosubstituted with a halogen atom or a $C_1$-$C_6$ alkyl group;

8) The compound according to 6) or 7), or a pharmaceutically acceptable salt thereof, wherein A is an unsubstituted or monosubstituted 5- or 6-membered aromatic heterocyclic ring that contains 1 to 3 heteroatoms selected from a sulfur atom, an oxygen atom, and a nitrogen atom, with one of those heteroatoms being a nitrogen atom adjacent to a ring-linking atom;

9) The compound according to 6) or 7), or a pharmaceutically acceptable salt thereof, wherein A is an unsubstituted or monosubstituted fused heterocyclic ring having a 5- or 6-membered aromatic heterocyclic ring that contains 1 to 3 heteroatoms selected from a sulfur atom, an oxygen atom, and a nitrogen atom, with one of those heteroatoms being a nitrogen atom adjacent to a ring-linking atom;

10) The compound according to 6) or 7), or a pharmaceutically acceptable salt thereof, wherein A is an unsubstituted or substituted aromatic heterocyclic ring selected from the following:

[Chemical formula 4]

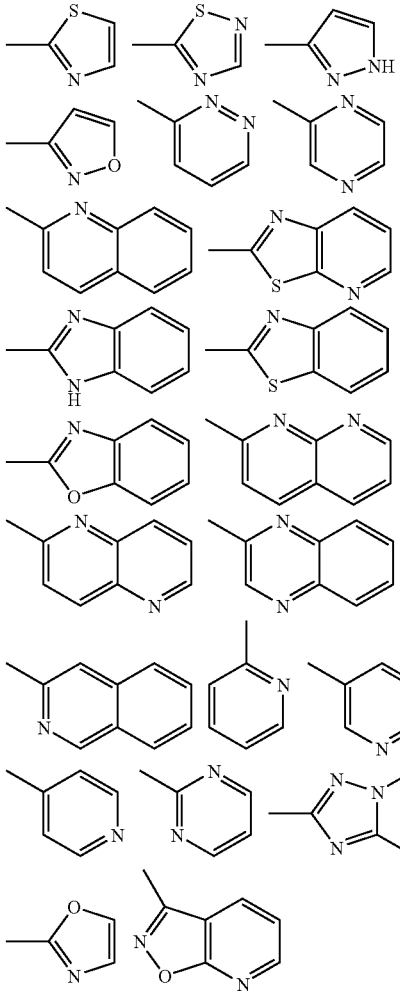

11) (−)-2-[4-(Cyclopropylsulfonyl)phenyl]-3-[(1α,3α,4α)-3,4-difluorocyclopentyl]-N-(thiazol-2-yl)propionamide or a pharmaceutically acceptable salt thereof;

12) (−)-2-[4-(Cyclopropylsulfonyl)phenyl]-3-[(1α,3α,4α)-3,4-difluorocyclopentyl]-N-(5-fluorothiazol-2-yl)propionamide or a pharmaceutically acceptable salt thereof;

13) (−)-2-[4-(Cyclopropylsulfonyl)phenyl]-3-[(1α,3α,4α)-3,4-difluorocyclopentyl]-N-(pyrazin-2-yl)propionamide or a pharmaceutically acceptable salt thereof;

14) (−)-2-[4-(Cyclopropylsulfonyl)phenyl]-3-[(1α,3α,4α)-3,4-difluorocyclopentyl]-N-(5-fluoropyridin-2-yl)propionamide or a pharmaceutically acceptable salt thereof;

15) A method of treating or preventing diabetes, comprising administering the compound according to any of 1) to 14), or a pharmaceutically acceptable salt thereof;

16) Use of the compound according to any of 1) to 14), or a pharmaceutically acceptable salt thereof, for manufacturing a medicament for treating or preventing diabetes;

17) A pharmaceutical composition comprising the compound according to any of 1) to 14), or a pharmaceutically acceptable salt thereof, and a pharmaceutically acceptable carrier;

18) A compound represented by the general formula (3):

[Chemical formula 5]

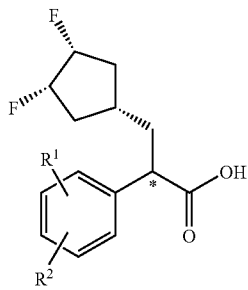

(3)

(wherein, the carbon atom marked with an * is in the R-configuration, $R^1$ represents a hydrogen atom, a halogen atom, an amino group, a hydroxyl group, a hydroxyamino group, a nitro group, a cyano group, a sulfamoyl group, a $C_1$-$C_6$ alkyl group, or a $C_1$-$C_6$ alkoxy group, and $R^2$ represents a $C_3$-$C_6$ cycloalkylsulfanyl group, a $C_3$-$C_6$ cycloalkylsulfinyl group, or a $C_3$-$C_6$ cycloalkylsulfonyl group); and 19) The compound according to 18), wherein $R^1$ is a hydrogen atom and $R^2$ is a $C_3$-$C_6$ cyclopropylsulfonyl group.

EFFECT OF THE INVENTION

According to the present invention, a compound is provided which has an excellent GK-activating effect or hypoglycemic effect, and fewer (less) side effects (for example, prolonged QT interval, hypoglycemia symptoms, and the like), which allows a pharmaceutical which is excellent in the treatment or prevention of diabetes, obesity and the like to be provided.

BEST MODE FOR CARRYING OUT THE INVENTION

As used herein, the term "halogen atom" refers to a fluorine atom, a chlorine atom, a bromine atom, or an iodine atom.

As used herein, the term "$C_1$-$C_6$ alkyl group" refers to a linear or branched alkyl group having 1 to 6 carbon atoms or a cycloalkyl group having 3 to 6 carbon atoms. Examples thereof may include a methyl group, an ethyl group, a propyl group, an isopropyl group, a butyl group, an isobutyl group, a sec-butyl group, a tert-butyl group, a cyclopropyl group, and a cyclobutyl group.

As used herein, the term "$C_1$-$C_6$ alkoxy group" refers to a linear or branched alkoxy group having 1 to 6 carbon atoms or a cycloalkoxy group having 3 to 6 carbon atoms. Examples thereof may include a methoxy group, an ethoxy group, a propoxy group, an isopropoxy group, a butoxy group, an isobutoxy group, a sec-butoxy group, a tert-butoxy group, a cyclopropxy group, and a cyclobutoxy group.

As used herein, the term "$C_3$-$C_6$ cycloalkylsulfanyl group" refers to a cyclic alkylsulfanyl group having 3 to 6 carbon atoms. Examples thereof may include a cyclopropylsulfanyl group, a cyclobutylsulfanyl group, and a cyclopentylsulfanyl group.

As used herein, the term "$C_3$-$C_6$ cycloalkylsulfinyl group" refers to a cyclic alkylsulfinyl group having 3 to 6 carbon atoms. Examples thereof may include a cyclopropylsulfinyl group, a cyclobutylsulfinyl group, and a cyclopentylsulfinyl group.

As used herein, the term "$C_3$-$C_6$ cycloalkylsulfonyl group" refers to a cyclic alkylsulfonyl group having 3 to 6 carbon atoms. Examples thereof may include a cyclopropylsulfonyl group, a cyclobutylsulfonyl group, and a cyclopentylsulfonyl group.

As used herein, the term "heteroaryl group" refers to a 5- or 6-membered aromatic heterocyclic ring that contains as the constituent atoms of the ring 1 to 3 heteroatoms selected from a sulfur atom, an oxygen atom, and a nitrogen atom. The heteroaryl group may optionally form a fused ring with a benzene ring or a 5- or 6-membered aromatic heterocyclic ring. Examples of preferred heteroaryl groups include heteroaryl groups having 1 to 3 heteroatoms selected from a sulfur atom, an oxygen atom, and a nitrogen atom, with one of those heteroatoms being a nitrogen atom adjacent to a ring-linking atom. Furthermore, the term "ring-linking atom" means an atom in the ring which binds to the nitrogen atom of the amide group. A carbon atom is preferred as such a ring-linking atom.

Examples of preferred heteroaryl groups include a thiazolyl group, a thiadiazolyl group, a pyrazolyl group, a pyridinyl group, a pyrazinyl group, a pyrimidinyl group, a pyridazinyl group, an oxazolyl group, an imidazolyl group, a triazinyl group, a benzothiazolyl group, a benzoxazolyl group, a benzoimidazolyl group, a pyridothiazolyl group, and a quinolinyl group. More preferred examples include a thiazolyl group, a pyrazolyl group, a pyrazinyl group, a pyridinyl group, thiazolo[5,4-b]pyridinyl group, a thiadiazolyl group, and a pyridothiazolyl group.

The term "substituted or unsubstituted heteroaryl group" denoted by A is preferably an unsubstituted or monosubstituted heteroaryl group. Examples of the substituent include a halogen atom, a $C_1$-$C_6$ alkyl group optionally substituted with a halogen atom, a $C_1$-$C_6$ alkoxy group optionally substituted with a halogen atom, a $C_1$-$C_3$ alkoxy-$C_1$-$C_3$ alkoxy group, a $C_1$-$C_6$ alkylsulfanyl group, a $C_1$-$C_6$ alkylsulfanyl-$C_1$-$C_6$ alkoxy group, a $C_1$-$C_6$ hydroxylalkyl group, a morpholino group, a $C_1$-$C_6$ hydroxylalkylsulfanyl group, a nitro group, a cyano group, and a group represented by the formula,

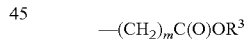

—$(CH_2)_mC(O)OR^3$ (wherein $R^3$ represents a hydrogen atom or a $C_1$-$C_6$ alkyl group and m is an integer of 0 to 2).

The compound of the present invention has an excellent GK-activating effect due to its stereostructure. Furthermore, when A is a heteroaryl group unsubstituted or monosubstituted with a halogen atom or a $C_1$-$C_6$ alkyl group, the compound of the present invention exhibits an excellent hypoglycemic effect. For example, compounds which have a different stereostructure for the cyclopentyl group and the fluorine atom bonded to the cyclopentyl group and/or a different configuration for the carbon atom marked with an * (for example, (+)-2-[4-(cyclopropylsulfonyl)phenyl]-3-[(1α,3α,4α)-3,4-difluorocyclopentyl]-N-(thiazol-2-yl)propionamide, (−)-2-[4-(cyclopropylsulfonyl)phenyl]-3-[(1β,3α,4α)-3,4-difluorocyclopentyl]-N-(thiazol-2-yl)propionamide, and (+)-2-[4-(cyclopropylsulfonyl)phenyl]-3-[(1β,3α,4α)-3,4-difluorocyclopentyl]-N-(thiazol-2-yl)propionamide) do not exhibit high hypoglycemic activity like that of the below-described compound 1 of the present invention.

Specific examples of the compound of the present invention include 2-[4-(cyclopropylsulfonyl)phenyl]-3-[(1α,3α, 4α)-3,4-difluorocyclopentyl]-N-(pyrazin-2-yl)propionamide, 2-[4-(cyclopropylsulfonyl)phenyl]-3-[(1α,3α,4α)-3,4-difluorocyclopentyl]-N-(5-fluorothiazol-2-yl)propionamide, 2-[4-(cyclopropylsulfonyl)phenyl]-3-[(1α,3α,4α)-3,4-difluorocyclopentyl]-N-(1-methyl-1H-pyrazol-3-yl)propionamide, N-(5-chloropyridin-2-yl)-2-[4-(cyclopropylsulfonyl)phenyl]-3-[(1α,3α,4α)-3,4-difluorocyclopentyl]propionamide, 2-[4-(cyclopropylsulfonyl)phenyl]-3-[(1α,3α,4α)-3,4-difluorocyclopentyl]-N-(5-fluoropyridin-2-yl)propionamide, 2-[4-(cyclopropylsulfonyl)phenyl]-3-[(1α,3α,4α)-3,4-difluorocyclopentyl]-N-(1-ethyl-1H-pyrazol-3-yl)propionamide, 2-[4-(cyclopropylsulfonyl)phenyl]-3-[(1α,3α,4α)-3,4-difluorocyclopentyl]-N-(5-methylpyrazin-2-yl)propionamide, 2-[4-(cyclopropylsulfonyl)phenyl]-3-[(1α,3α,4α)-3,4-difluorocyclopentyl]-N-(1-{[(R)-2,2-dimethyl-1,3-dioxolan-4-yl]methyl}-1H-pyrazol-3-yl)propionamide, 2-[4-(cyclopropylsulfonyl)phenyl]-3-[(1α,3α,4α)-3,4-difluorocyclopentyl]-N-[1-[(R)-2,3-dihydroxypropyl]-1H-pyrazol-3-yl)propionamide, 2-[4-(cyclopropylsulfonyl)phenyl]-3-[(1α,3α,4α)-3,4-difluorocyclopentyl]-N-(1-{[(S)-2,2-dimethyl-1,3-dioxolan-4-yl]methyl}-1H-pyrazol-3-yl)propionamide, 2-[4-(cyclopropylsulfonyl)phenyl]-3-[(1α,3α,4α)-3,4-difluorocyclopentyl]-N-{1-[(S)-2,3-dihydroxypropyl]-1H-pyrazol-3-yl}propionamide, 2-[4-(cyclopropylsulfonyl)phenyl]-3-[(1α,3α,4α)-3,4-difluorocyclopentyl]-N-[1-(difluoromethyl)-1H-pyrazol-3-yl]propionamide, 2-[4-(cyclopropylsulfonyl)phenyl]-3-[(1α,3α,4α)-3,4-difluorocyclopentyl]-N-[1-(2,2,2-trifluoroethyl)-1H-pyrazol-3-yl]propionamide, 2-[4-(cyclopropylsulfonyl)phenyl]-3-[(1α,3α,4α)-3,4-difluorocyclopentyl]-N-[5-(2-methoxyethoxy)thiazol[5,4-b]pyridin-3-yl)propionamide, (R)—N-(5-cyclopropylpyridin-2-yl)-2-[4-(cyclopropylsulfonyl)phenyl]-3-[(1α,3α,4α)-3,4-difluorocyclopentyl]propionamide, (R)-2-[4-(cyclopropylsulfonyl)phenyl]-3-[(1α,3α,4α)-3,4-difluorocyclopentyl]-N-[5-(ethylthio)pyridin-2-yl)propionamide, (R)-2-[4-(cyclopropylsulfonyl)phenyl]-3-[(1α,3α,4α)-3,4-difluorocyclopentyl]-N-[5-(methylthio)pyridin-2-yl)propionamide, (R)-2-[4-(cyclopropylsulfonyl)phenyl]-3-[(1α,3α,4α)-3,4-difluorocyclopentyl]-N-[5-(2-methoxyethoxy)pyrazin-2-yl)propionamide, (R)-2-[4-(cyclopropylsulfonyl)phenyl]-3-[(1α,3α,4α)-3,4-difluorocyclopentyl]-N-[5-(2-methyl)ethoxypyrazin-2-yl)propionamide, (R)-2-[4-(cyclopropylsulfonyl)phenyl]-3-[(1α,3α,4α)-3,4-difluorocyclopentyl]-N-(5-ethylpyrazin-2-yl)propionamide, (R)-2-[4-(cyclopropylsulfonyl)phenyl]-3-[(1α,3α,4α)-3,4-difluorocyclopentyl]-N-[5-[2-(methylthio)ethoxy]pyrazin-2-yl]propionamide, (R)-2-[4-(cyclopropylsulfonyl)phenyl]-3-[(1α,3α,4α)-3,4-difluorocyclopentyl]-N-(5-methoxypyrazin-2-yl)propionamide, (R)-2-[4-(cyclopropylsulfonyl)phenyl]-3-[(1α,3α,4α)-3,4-difluorocyclopentyl]-N-[1-(2-hydroxy-2-methylpropyl)-1H-pyrazol-3-yl]propionamide, (R)-2-[4-(cyclopropylsulfonyl)phenyl]-3-[(1α,3α,4α)-3,4-difluorocyclopentyl]-N-(6-morpholinobenzo[d]thiazol-2-yl)propionamide, isopropyl 2-{(R)-2-[4-(cyclopropylsulfonyl)phenyl]-3-[(1α,3α,4α)-3,4-difluorocyclopentyl]propionamide}benzo[d]thiazol-6-carbonate, 2-methoxyethyl 2-{(R)-2-[4-(cyclopropylsulfonyl)phenyl]-3-[(1α,3α,4α)-3,4-difluorocyclopentyl]propionamide}benzo[d]thiazol-6-carbonate, (R)-2-[4-(cyclopropylsulfonyl)phenyl]-3-[(1α,3α,4α)-3,4-difluorocyclopentyl]-N-(thiazol[5,4-b]pyridin-2-yl)propionamide, (R)-2-[4-(cyclopropylsulfonyl)phenyl]-3-[(1α,3α,4α)-3,4-difluorocyclopentyl]-N-{4-[(4RS)-2,2-dimethyl-1,3-dioxolan-4-yl]thiazol-2-yl}propionamide, (R)-2-[4-(cyclopropylsulfonyl)phenyl]-3-[(1α,3α,4α)-3,4-difluorocyclopentyl]-N-(4-methylthiazol-2-yl)propionamide, (R)-2-[4-(cyclopropylsulfonyl)phenyl]-3-[(1α,3α,4α)-3,4-difluorocyclopentyl]-N-(5-methylthiazol-2-yl)propionamide, (R)—N-{[4-(2,2-dimethyl)ethyl]thiazol-2-yl}-2-[4-(cyclopropylsulfonyl)phenyl]-3-[(1α,3α,4α)-3,4-difluorocyclopentyl]propionamide, (R)—N-(5-bromothiazol-2-yl)-2-[4-(cyclopropylsulfonyl)phenyl]-3-[(1α,3α,4α)-3,4-difluorocyclopentyl]propionamide, (R)-2-[4-(cyclopropylsulfonyl)phenyl]-3-[(1α,3α,4α)-3,4-difluorocyclopentyl]-N-(1,2,4-thiazol-5-yl)propionamide, (R)-2-[4-(cyclopropylsulfonyl)phenyl]-3-[(1α,3α,4α)-3,4-difluorocyclopentyl]-N-(3-ethyl-1,2,4-thiazol-5-yl)propionamide, (R)-2-[4-(cyclopropylsulfonyl)phenyl]-3-[(1α,3α,4α)-3,4-difluorocyclopentyl]-N-(3-morpholino-1,2,4-thiazol-5-yl)propionamide, ethyl 2-{6-[(R)-2-[4-(cyclopropylsulfonyl)phenyl]-3-[(1α,3α,4α)-3,4-difluorocyclopentyl]propionamide]pyridin-3-ylthio}-2-methylpropionate, (R)-2-[4-(cyclopropylsulfonyl)phenyl]-3-[(1α,3α,4α)-3,4-difluorocyclopentyl]-N-{5-[2-(tetrahydro-2H-pyran-2-yloxy)ethoxy]pyrazin-2-yl}propionamide, (R)-2-[4-(cyclopropylsulfonyl)phenyl]-3-[(1α,3α,4α)-3,4-difluorocyclopentyl]-N-[5-(2-hydroxyethoxy)pyrazin-2-yl]propionamide, (R)-2-[4-(cyclopropylsulfonyl)phenyl]-3-[(1α,3α,4α)-3,4-difluorocyclopentyl]-N-[5-(3-methoxypropoxy)pyrazin-2-yl]propionamide, (R)-2-[4-(cyclopropylsulfonyl)phenyl]-3-[(1α,3α,4α)-3,4-difluorocyclopentyl]-N-[5-(2-ethoxyethoxy)pyrazin-2-yl]propionamide, (R)-2-[4-(cyclopropylsulfonyl)phenyl]-3-[(1α,3α,4α)-3,4-difluorocyclopentyl]-N-{5-[(4S)-2,2-dimethyl-1,3-dioxolan-4-yl]pyrazin-2-yl}propionamide, (R)-2-[4-(cyclopropylsulfonyl)phenyl]-3-[(1α,3α,4α)-3,4-difluorocyclopentyl]-N-{5-[(2S)-1,2-dihydroxyethyl]pyrazin-2-yl}propionamide, (R)-2-[4-(cyclopropylsulfonyl)phenyl]-3-[(1α,3α,4α)-3,4-difluorocyclopentyl]-N-[5-[(4R)-2,2-dimethyl-1,3-dioxolan-4-yl]pyrazin-2-yl]propionamide, (R)-2-[4-(cyclopropylsulfonyl)phenyl]-3-[(1α,3α,4α)-3,4-difluorocyclopentyl]-N-{5-[(2R)-1,2-dihydroxyethyl]pyrazin-2-yl}propionamide, (R)-2-[4-(cyclopropylsulfonyl)phenyl]-3-[(1α,3α,4α)-3,4-difluorocyclopentyl]-N-[5-(2-hydroxyethylthio)pyrazin-2-yl]propionamide, (R)-2-[4-(cyclopropylsulfonyl)phenyl]-3-[(1α,3α,4α)-3,4-difluorocyclopentyl]-N-(3,5-dimethylpyrazin-2-yl)propionamide, (R)-2-[4-(cyclopropylsulfonyl)phenyl]-3-[(1α,3α,4α)-3,4-difluorocyclopentyl]-N-[1-(2-fluoroethyl)-1H-pyrazol-3-yl]propionamide, (R)-2-[4-(cyclopropylsulfonyl)phenyl]-3-[(1α,3α,4α)-3,4-difluorocyclopentyl]-N-[1-(2-methyl)ethyl-1H-pyrazol-3-yl]propionamide, (R)-2-[4-(cyclopropylsulfonyl)phenyl]-3-[(1α,3α,4α)-3,4-difluorocyclopentyl]-N-[1-(2-hydroxyethyl)-1H-pyrazol-3-yl]propionamide, (R)-2-[4-(cyclopropylsulfonyl)phenyl]-3-[(1α,3α,4α)-3,4-difluorocyclopentyl]-N-(isoxazol-3-yl)propionamide, (R)-2-[4-(cyclopropylsulfonyl)phenyl]-3-[(1α,3α,4α)-3,4-difluorocyclopentyl]-N-(6-methoxybenzo[d]thiazol-2-yl)propionamide, (R)—N-(benzo[d]thiazol-2-yl)-2-[4-(cyclopropylsulfonyl)phenyl]-3-[(1α,3α,4α)-3,4-difluorocyclopentyl]propionamide, (R)-2-[4-(cyclopropylsulfonyl)phenyl]-3-[(1α,3α,4α)-3,4-difluorocyclopentyl]-N-[6-(difluoromethoxy)benzo[d]thiazol-2-yl]propionamide, (R)—N-(5-butoxythiazol[5,4-b]pyridin-2-yl)-2-[4-(cyclopropylsulfonyl)phenyl]-3-[(1α,3α,4α)-3,4-difluorocyclopentyl]propionamide, ethyl 2-{2-[(R)-2-[4-(cyclopropylsulfonyl)phenyl]-3-[(1α,3α,4α)-3,4-difluorocyclopentyl]propionamide]thiozole[5,4-b]pyridin-5-yloxy}acetate, (R)-2-[4-(cyclopropylsulfonyl)phenyl]-3-[(1α,3α,4α)-3,4-difluorocyclopentyl]-N-(1-methyl-1H- benzo[d]imidazol-2-yl)propionamide, (R)-2-[4-(cyclopropylsulfonyl)phenyl]-3-[(1α,3α,4α)-3,4-difluorocyclopentyl]-N-(isoxazole[5,4-b]pyridine-3-yl) propionamide, (R)-2-[4-(cyclopropylsulfonyl)phenyl]-3-[(1α,3α,4α)-3,4-difluorocyclopentyl]-N-[4-(2,2-dimethyl-1,3-dioxan-5-yl)thiazol-2-yl]propionamide, (R)-2-[4-(cyclopropylsulfonyl)phenyl]-3-[(1α,3α,4α)-3,4-difluorocyclopentyl]-N-[4-(1,3-dihydroxypropan-2-yl) thiazol-2-yl]propionamide, (R)-2-[4-(cyclopropylsulfonyl) phenyl]-3-[(1α,3α,4α)-3,4-difluorocyclopentyl]-N-[4-(2-hydroxyethyl)thiazol-2-yl]propionamide, (R)-2-[4-(cyclopropylsulfonyl)phenyl]-3-[(1α,3α,4α)-3,4-difluorocyclopentyl]-N-[3-phenyl-1,2,4-thiazol-5-yl] propionamide, (R)-2-[4-(cyclopropylsulfonyl)phenyl]-3-[(1α,3α,4α)-3,4-difluorocyclopentyl]-N-[3-(pyridin-4-yl)-1,2,4-thiazol-5-yl]propionamide, (R)-2-[4-(cyclopropylsulfonyl)phenyl]-3-[(1α,3α,4α)-3,4-difluorocyclopentyl]-N-(3-methyl-1,2,4-thiazol-5-yl) propionamide, and (R)-2-[4-(cyclopropylsulfonyl)phenyl]-3-[(1α,3α,4α)-3,4-difluorocyclopentyl]-N-(3-methoxy-1,2,4-thiazol-5-yl)propionamide.

In the present invention, unless stated otherwise, the (−) sign of optical rotation means that the sign of optical rotation of the compound measured by the sodium D line with chloroform as a solvent is negative (−).

A "pharmaceutically acceptable salt thereof" may be an arbitrary salt of an inorganic or organic acid, such as hydrochloric acid, hydrobromic acid, nitric acid, sulfuric acid, phosphoric acid, citric acid, formic acid, maleic acid, acetic acid, succinic acid, and tartaric acid.

The compound represented by the general formula (1) of the present invention can be produced according to the following production steps, for example, with a compound represented by the general formula (3) as an intermediate.

[Chemical formula 6]

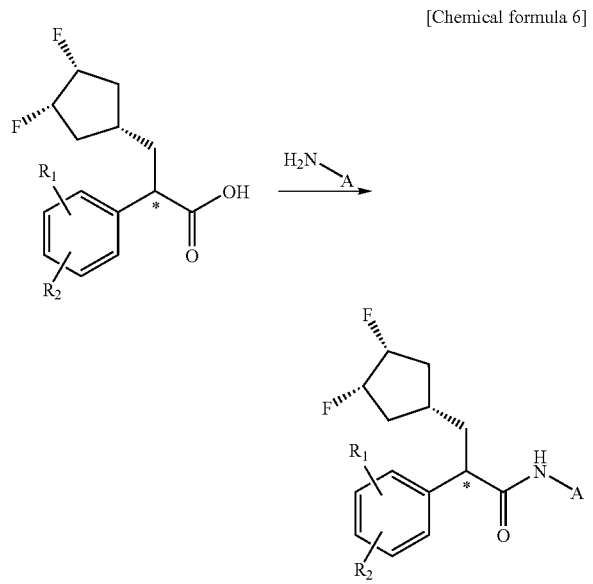

(wherein *, $R^1$, $R^2$, and A are as defined above.)

In this step, the compound represented by the general formula (1) is produced by reacting the compound represented by the general formula (3) and a heteroarylamine in the presence of a suitable reagent.

This reaction can be carried out by a method in which a general condensation agent is used, or by appropriately employing an active ester method, a mixed acid anhydride method, an acid halide method, or a carbodiimide method. Examples of reagents which may be used in such reactions include thionyl chloride, oxalyl chloride, N,N'-dicyclohexylcarbodiimide, N,N'-diisopropylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazol-1-yl-oxy-tris(dimethylamino)phosphonium hexafluorophosphate, and N-bromosuccinimide/triphenylphosphine. In this step, a base or a condensation aid may also be used with the above-described reagent. The base used at this stage may be any base as long as it is not involved in the reaction. For example, the reaction may be carried out in the presence of a base such as an alkali metal alkoxide such as sodium methoxide and sodium ethoxide, an alkali metal hydride such as sodium hydride and potassium hydride, an alkali metal organic base such as n-butyllithium, lithium bis(trimethylsilyl)amide, sodium bis(trimethylsilyl)amide, and potassium bis(trimethylsilyl)amide, a tertiary organic base such as triethylamine, diisoproprlethylamine, pyridine, N-methylmorpholine, imidazole, N-methylpyrrolidine, N-methylpiperidine, 1,5-diazabicyclo[4.3.0]nona-5-ene, and 1,8-diazabicyclo[5.4.0]undec-7-ene, or an inorganic base such as potassium carbonate, and sodiumbicarbonate. Furthermore, examples of condensation aids which may be used include N-hydroxybenzotriazole hydrate, N-hydroxysuccinimide, N-hydroxy-5-norbornene-2,3-dicarboxylmide, 3-hydroxy-3,4-dihydro-4-oxo-1,2,3-benzotriazole, and pentafluorophenol. Any solvent may be used as the reaction solvent, as long as it is not involved in the reaction. Examples of reaction solvents which may be preferably used include hydrocarbon solvents such as hexane, cyclohexane, benzene, toluene, and xylene, halogenated hydrocarbon solvents such as dichloromethane, 1,2-dichloroethane, chloroform, and carbon tetrachloride, ether solvents such as diethyl ether, tetrahydrofuran, and 1,4-dioxane, and aprotic polar solvents such as acetonitrile, propionitrile, nitromethane, nitroethane, N,N-dimethylformamide, N-methylpiperidine, sulfolane, and dimethylsulfoxide. Usually, the reaction smoothly proceeds at −78 to 200° C.

One aspect of the present invention relates to a pharmaceutical having the compound represented by the formula (1), or a pharmaceutically acceptable salt thereof, as an active ingredient. The pharmaceutical of the present invention has a GK-activating effect or a hypoglycemic effect. Therefore, the pharmaceutical of the present invention is useful in the treatment or prevention of type I diabetes, type II diabetes, hyperlipidemia (hyper-LDL cholesteremia, hypertriglyceridemia, and hypo-HDL cholesteremia), obesity, insulin resistance, impaired glucose tolerance, metabolic syndrome and the like.

The pharmaceutical of the present invention may be administered orally, or via a non-oral route, for example intrarectally, subcutaneously, intravenously, intramuscularly, transdermally and the like.

To use as a pharmaceutical, the compound of the present invention, or a pharmaceutically acceptable salt thereof, may be in the form of any of a solid composition, a liquid composition, or some other composition. The optimum form is selected as necessary. The pharmaceutical of the present invention can be produced by mixing with a carrier which is pharmaceutically acceptable with the compound of the present invention. Specifically, the compound of the present invention can be prepared by ordinary formulation techniques as a tablet, pill, capsule, granule, powder, powdered drug, liquid, emulsion, suspension, injection and the like, by adding common excipients, fillers, binders, disintegrating agents, coating agents, sugar coating agents, pH adjusting agents, dissolving agents, or aqueous or non-aqueous solvents.

While the dose of the compound of the present invention, or a pharmaceutically acceptable salt thereof, may vary depending on the disorder, symptoms, body weight, age, sex, administration route and the like, for an adult, for oral administration a preferred dose is about 0.01 to about 1,000 mg/kg body weight/day, and a more preferred dose is about 0.5 to about 200 mg/kg body weight/day. This amount can be administered once per day, or divided up into several times per day.

The compound of the present invention, or a pharmaceutically acceptable salt thereof, can optionally be used with one or more kinds of compound other than a GK-activating compound. For example, the compound of the present invention, or a pharmaceutically acceptable salt thereof, can be suitably used in combination with one or more of an antidiabetic agent or an antihyperglycemic agent, including sulfonylureas, biguanides, glucagon antagonists, α-glucosidase inhibitors, insulin secretagogues, and insulin sensitizers, or an anti-obesity agent.

Examples of the sulfonylurea include glyburide, glimepiride, glipyride, glipizide, chlorpropamide, gliclazide, glisoxepide, acetohexamide, glibornuride, tolbutamide, tolazamide, carbutamide, gliquidone, glyhexamide, phenbutamide, and tolcyclamide. Examples of the biguanide include metformin, phenformin, and buformin. Examples of the glucagon antagonist include a peptide or non-peptide glucagon antagonist. Examples of the α-glucosidase inhibitor include acarbose, voglibose, and miglitol. Examples of the insulin sensitizer include troglitazone, rosiglitazone, pioglitazone, and ciglitazone. Examples of the anti-obesity agent include sibutramine, and orlistat. The compound of the present invention, or a pharmaceutically acceptable salt thereof, may be administered simultaneously, sequentially, or separately to the other anti-diabetic agents or anti-hyperglycemic agents, or the anti-obesity agents.

Example 1

Ethyl(±)-2-[4-(cyclopropylsulfonyl)phenyl]-3-[(1α, 3α,4α)-3,4-difluorocyclopentyl]propionate (Method I)

[Chemical formula 7]

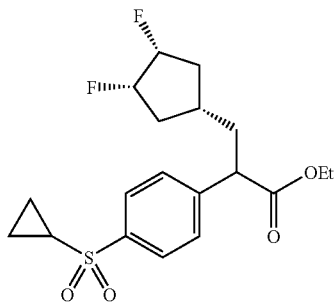

First Step

Ethyl[4-(cyclopropylthio)phenyl]acetate

[4-(Cyclopropylthio)phenyl]acetic acid (13.1 g) was dissolved into ethanol (52 mL). Then, thionyl chloride (5.51 mL) was added dropwise while cooling by an ice bath, and the resulting mixture was stirred for 90 minutes at room temperature. This reaction mixture was concentrated under reduced pressure, and the resulting residue was dissolved in ethyl acetate (125 mL). This ethyl acetate solution was washed with water (4×25 mL) and then a saturated aqueous sodium carbonate solution (25 mL). The resulting mixture was dried over anhydrous sodium sulfate, then filtered and concentrated under reduced pressure. The resulting residue was purified by silica gel column chromatography (eluant; hexane:ethyl acetate=3:1) to obtain ethyl[4-(cyclopropylthio)phenyl]acetate (15.5 g).

$^1$H NMR (400 MHz, CDCl$_3$) δ 0.66-0.71 (m, 2H), 1.02-1.09 (m, 2H), 1.25 (t, J=7.4 Hz, 3H), 2.14-2.21 (m, 1H), 3.57 (s, 2H), 4.15 (q, J=7.4 Hz, 2H), 7.18-7.23 (m, 2H), 7.30-7.35 (m, 2H).

Second Step

Ethyl[4-(cyclopropylsulfonyl)phenyl]acetate

Ethyl[4-(cyclopropylthio)phenyl]acetate (14.2 g) was dissolved in dichloromethane (200 mL). Meta-chloroperbenzoic acid (35.1 g) was added thereto while cooling by an ice bath, and then the resulting mixture was stirred for 1 hour at room temperature. Insoluble matter in this reaction mixture was filtered off, and the filtrate was then diluted with dichloromethane (280 mL). This dichloromethane solution was washed with a 10% aqueous sodium bisulfite solution (2×140 mL), a saturated aqueous sodium bicarbonate solution (2×140 mL), and saturated brine (140 mL) in that order. The resulting mixture was dried over anhydrous sodium sulfate, then filtered and concentrated under reduced pressure. The resulting residue was purified by silica gel column chromatography (eluant; hexane:ethyl acetate=1:1) to obtain ethyl [4-(cyclopropylsulfonyl)phenyl]acetate (15.0 g).

$^1$H NMR (400 MHz, CDCl$_3$) δ 1.00-1.07 (m, 2H), 1.27 (t, J=7.3 Hz, 3H), 1.33-1.39 (m, 2H), 2.41-2.49 (m, 1H), 3.71 (s, 2H), 4.18 (q, J=7.3 Hz, 2H), 7.45-7.52 (m, 2H), 7.83-7.90 (m, 2H).

Third Step

Ethyl(±)-2-[4-(cyclopropylsulfonyl)phenyl]-3-[(1α, 3α,4α)-3,4-difluorocyclopentyl]propionate N,N-dimethylpropyleneurea (3.9 mL) was dissolved in tetrahydrofuran (75 mL), and lithium bis(trimethylsilyl)amide (1 mol/L tetrahydrofuran solution, 8.20 mL) was added thereto at −78° C. A solution of ethyl[4-(cyclopropylsulfonyl) phenyl]acetate (2.00 g) in tetrahydrofuran (10 mL) was then added dropwise. This reaction mixture was stirred for 1 hour at −78° C. (1α,3α,4α)-(3,4-difluorocyclopentyl)methyl iodide (2.02 g) was then added to the reaction mixture at −78° C., and then the mixture was stirred for a further 16 hours at room temperature. A saturated aqueous ammonium chloride solution (20 mL) was added to the reaction mixture and the mixture was extracted with ethyl acetate (3×20 mL). The ethyl acetate extract was washed with saturated brine (20 mL), dried over anhydrous sodium sulfate, then filtered and concentrated under reduced pressure. The resulting residue was purified by silica gel column chromatography (eluant;

hexane:dioxane=2:1) to obtain ethyl (±)-2-[4-(cyclopropylsulfonyl)phenyl]-3-[(1α,3α,4α)-3,4-difluorocyclopentyl] propionate (1.45 g).

MS (EI⁺) m/z: 386 (M⁺)

HRMS (EI⁺) for $C_{19}H_{24}F_2O_4S$ (M⁺): calcd., 386.1363; found, 386.1389.

¹H NMR (400 MHz, CDCl₃) δ 1.02-1.07 (m, 2H), 1.23 (d, J=7.3 Hz, 3H), 1.34-1.39 (m, 2H), 1.63-1.82 (m, 3H), 1.93-2.00 (m, 1H), 2.08-2.19 (m, 2H), 2.23-2.30 (m, 1H), 2.43-2.49 (m, 1H), 3.65 (t, J=7.9 Hz, 1H), 4.07-4.21 (m, 2H), 4.73-4.92 (m, 2H), 7.49-7.51 (m, 2H), 7.85-7.88 (m, 2H).

Example 2

Ethyl(±)-2-[4-(cyclopropylsulfonyl)phenyl]-3-[(1α,3α,4α)-3,4-difluorocyclopentyl]propionate (Method II)

[Chemical formula 8]

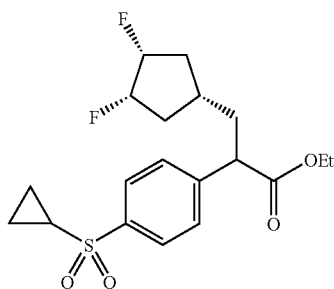

First Step

Ethyl 2-[4-(cyclopropylthio)phenyl]-3-[(1α,3α,4α)-3,4-difluorocyclopentyl]acrylate (1α,3α,4α)-(3,4-Difluorocyclopentyl)methylphosphonium iodide (9.15 g) was suspended in tetrahydrofuran (28 mL), and lithium bis(trimethylsilyl) amide (1 mol/L tetrahydrofuran solution, 18.0 mL) was added to the resulting suspension while cooling by an ice bath. The resulting mixture was then stirred for 1 hour at the same temperature. Next, ethyl[4-(cyclopropylthio) phenyl]oxoacetate (3.75 g) in tetrahydrofuran (18 mL) was added dropwise to the reaction mixture while cooling by an ice bath. The reaction mixture was stirred for 1 hour at the same temperature, and then stirred for a further 5 hours at room temperature. Water (34 mL) was added to the reaction mixture, and the pH of the mixture was adjusted to pH 6 with 1 mol/L hydrochloric acid. Then, the tetrahydrofuran was removed by distillation under reduced pressure, and the residue product was extracted with ethyl acetate (2×90 mL). The ethyl acetate extracts were combined, and was washed with saturated brine, dried over anhydrous sodium sulfate, then filtered and concentrated under reduced pressure. The resulting residue was purified by silica gel column chromatography (eluant; hexane:ethyl acetate=4:1) to obtain ethyl 2-[4-(cyclopropylthio) phenyl]-3-[(1α,3α,4α)-3,4-difluorocyclopentyl]acrylate (4.72 g).

¹H NMR (400 MHz, CDCl₃) δ 0.68-0.73 (m, 2H), 1.07-1.12 (m, 2H), 1.24-1.33 (m, 3H), 1.90-2.40 (m, 5H), 2.58-2.69 (m, 0.7H), 3.20-3.27 (m, 0.3H), 4.19-4.31 (m, 2H), 4.73-5.00 (m, 2H), 6.13 (d, J=9.8 Hz, 0.3H), 6.97 (d, J=10.4 Hz, 0.7H), 7.04-7.06 (m, 1.3H), 7.21-7.25 (m, 0.7H), 7.31-7.37 (m, 2H).

Second Step

Ethyl 2-[4-(cyclopropylsulfonyl) phenyl]-3-[(1α,3α,4α)-3,4-difluorocyclopentyl]acrylate Ethyl 2-[4-(cyclopropylthio) phenyl]-3-[(1α,3α,4α)-3,4-difluorocyclopentyl]acrylate (4.72 g) was dissolved in dichloromethane (50 mL), and m-chloroperbenzoic acid (7.83 g) was added thereto while cooling by an ice bath. The resulting mixture was stirred for 1 hour at the same temperature, and then for a further 1 hour at room temperature. Insoluble matter in this reaction mixture was filtered off, and the filtrate was diluted with dichloromethane (50 mL). This dichloromethane solution was washed with a 10% aqueous sodium sulfite solution (2×20 mL), a saturated aqueous sodium bicarbonate solution (2×20 mL), and water (20 mL). The resulting mixture was dried over anhydrous sodium sulfate, then filtered and concentrated under reduced pressure. The resulting residue was purified by silica gel column chromatography (eluant; hexane:ethyl acetate=1:1) to obtain ethyl 2-[4-(cyclopropylsulfonyl)phenyl]-3-[(1α,3α,4α)-3,4-difluorocyclopentyl]acrylate (5.01 g).

¹H NMR (400 MHz, CDCl₃) δ 1.02-1.10 (m, 2H), 1.29-1.34 (m, 3H), 1.35-1.41 (m, 2H), 1.88-2.16 (m, 3H), 2.33-2.58 (m, 2.5H), 3.35-3.45 (m, 0.5H), 4.22-4.32 (m, 2H), 4.75-5.05 (m, 2H), 6.29 (d, J=9.8 Hz, 0.5H), 7.08 (d, J=10.4 Hz, 0.5H), 7.32-7.35 (m, 1.1H), 7.48-7.51 (m, 0.9H), 7.85-7.88 (m, 0.9H), 7.89-7.92 (m, 1.1H).

Third Step

Ethyl(±)-2-[4-(cyclopropylsulfonyl)phenyl]-3-[(1α,3α,4α)-3,4-difluorocyclopentyl]propionate Ethyl 2-[4-(cyclopropylsulfonyl)phenyl]-3-[(1α,3α,4α)-3,4-difluorocyclopentyl]acrylate (5.01 g) was dissolved in ethyl acetate (50 mL), and a suspension of 10% palladium carbon (875 mg) in ethanol (9 mL) was added thereto. The resulting mixture was stirred for 3 hours at room temperature under a hydrogen pressure of 2.94×10⁵ Pa. The catalyst in the reaction mixture was filtered off using a Celite pad, and the catalyst and the Celite pad were washed with ethyl acetate. The filtrate and the washing solution were combined, and the resulting mixture was then concentrated under reduced pressure to obtain ethyl (±)-2-[4-(cyclopropylsulfonyl)phenyl]-3-[(1α,3α,4α)-3,4-difluorocyclopentyl]propionate (5.04 g).

The results from measuring various kinds of spectral data showed that the present compound matched the compound obtained in the third step of Example 1.

Example 3

(±)-2-[4-(Cyclopropylsulfonyl)phenyl]-3-[(1α,3α,4α)-3,4-difluorocyclopentyl]propionic acid

[Chemical formula 9]

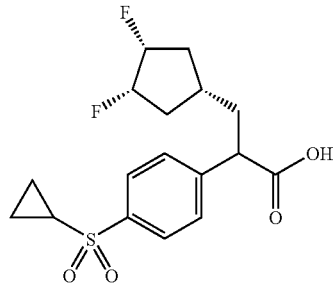

Method A: Ethyl 2-[4-(cyclopropylsulfonyl)phenyl]-3-[(1α,3α,4α)-3,4-difluorocyclopentyl]propionate (5.04 g) was dissolved in ethanol (50 mL). A 2 mol/L aqueous sodium hydroxide solution (13.0 mL) was added to this solution, followed by stirring for 90 minutes at 65° C. Ethanol in the reaction mixture was removed by distillation under reduced pressure, and the pH of the resulting residue product was adjusted to pH 1 with 4 mol/L hydrochloric acid. The mixture was then extracted with ethyl acetate (2×100 mL). The ethyl acetate extracts were combined, and the resulting mixture was washed with saturated brine (2×30 mL), dried over anhydrous sodium sulfate, then filtered and concentrated under reduced pressure. The resulting residue was purified by silica gel column chromatography (eluant; ethyl acetate) to obtain (±)-2-[4-(cyclopropylsulfonyl)phenyl]-3-[(1α,3α,4α)-3,4-difluorocyclopentyl]propionic acid (4.24 g).

Method B: Ethyl(±)2-[4-(cyclopropylsulfonyl)phenyl]-3-[(1α,3α,4α)-3,4-difluorocyclopentyl]propionate (1.40 g) was dissolved in a tetrahydrofuran-methanol mixed solution (1:1, 36 mL), and water (18 mL) was added to the solution. To the resulting mixture lithium hydroxide (435 mg) was added, and the mixture was stirred for 30 minutes at room temperature. This reaction mixture was washed with a hexane-ethyl acetate mixed solution (1:1, 30 mL), and the pH of the mixture was then adjusted to pH 1 with 2 mol/L hydrochloric acid. The mixture was then extracted with ethyl acetate (2×30 mL). The ethyl acetate extracts were combined, and the resulting mixture was dried over anhydrous sodium sulfate, then filtered and concentrated under reduced pressure to obtain (±)-2-[4-(cyclopropylsulfonyl)phenyl]-3-[(1α,3α,4α)-3,4-difluorocyclopentyl]propionic acid (1.12 g).

MS (EI$^+$) m/z: 358 (M$^+$).

HRMS (EI$^+$) for $C_{17}H_{20}F_2O_4S$ (M$^+$): calcd., 358.1050; found, 358.1014.

$^1$H NMR (400 MHz, CDCl$_3$) δ 1.02-1.08 (m, 2H), 1.34-1.38 (m, 2H), 1.62-1.85 (m, 3H), 1.96-2.03 (m, 1H), 2.12-2.18 (m, 2H), 2.25-2.32 (m, 1H), 2.42-2.49 (m, 1H), 3.69 (t, J=7.9 Hz, 1H), 4.73-4.91 (m, 2H), 7.51 (d, J=7.9 Hz, 2H), 7.87 (d, J=7.9 Hz, 2H).

Example 4

(−)-2-[4-(Cyclopropylsulfonyl)phenyl]-3-[(1α,3α,4α)-3,4-difluorocyclopentyl]propionic acid

[Chemical formula 10]

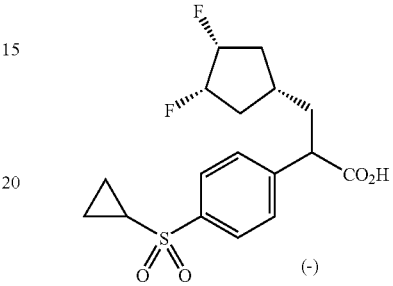

(±)-2-[4-(Cyclopropylsulfonyl)phenyl]-3-[(1α,3α,4α)-3,4-difluorocyclopentyl]propionic acid (1.00 g) was dissolved in a hexane-ethanol mixed solution (1:1), and the resulting mixture was separated by high-performance liquid chromatography (Chiralpak 1A (manufactured by Daicel Chemical Industries Ltd.), Φ 2.0 cm×25 cm, hexane:tert-butyl methyl ether:ethanol:trifluoroacetic acid=67:23:10:0.1, flow rate 20 mL/min, UV=254 nm). A fraction with a retention time of 14 minutes was concentrated under reduced pressure. To the resulting residue a saturated aqueous sodium bicarbonate solution (20 mL) was added. This solution was then washed with ethyl acetate (20 mL). The pH of the aqueous layer was adjusted to pH 1 with 1 mol/L hydrochloric acid. The resultant crystals were collected by filtration to obtain (−)-2-[4-(cyclopropylsulfonyl)phenyl]-3-[(1α,3α,4α)-3,4-difluorocyclopentyl]propionic acid (466 mg). Another fraction with a retention time of 18.6 minutes was concentrated under reduced pressure. To the resulting residue a saturated aqueous sodium bicarbonate solution (20 mL) was added. This solution was then washed with ethyl acetate (20 mL). The pH of the aqueous layer was adjusted to pH 1 with 1 mol/L hydrochloric acid. The resultant crystals were collected by filtration to obtain (+)-2-[4-(cyclopropylsulfonyl)phenyl]-3-[(1α,3α,4α)-3,4-difluorocyclopentyl]propionic acid (458 mg).

(−)-form:

MS (EI$^+$) m/z: 358 (M$^+$).

HRMS (EI$^+$) for $C_{17}H_{20}F_2O_4S$ (M$^+$): calcd., 358.1050; found, 358.1088.

$^1$H NMR (400 MHz, DMSO-d6) δ 1.00-1.05 (m, 2H), 1.08-1.12 (m, 2H), 1.42-1.75 (m, 3H), 1.78-1.86 (m, 1H), 1.95-2.18 (m, 3H), 2.81-2.88 (m, 1H), 3.71 (t, J=7.3 Hz, 1H), 4.75-4.95 (m, 2H), 7.58 (d, J=8.6 Hz, 2H), 7.84 (d, J=8.6 Hz, 2H), 12.63 (brs, 1H).

(+)-form:

MS (EI$^+$) m/z: 358 (M$^+$).

HRMS (EI$^+$) for $C_{17}H_{20}F_2O_4S$ (M$^+$): calcd., 358.1050; found, 358.1019.

$^1$H NMR (400 MHz, DMSO-d6) δ 1.00-1.05 (m, 2H), 1.08-1.12 (m, 2H), 1.42-1.75 (m, 3H), 1.78-1.86 (m, 1H), 1.95-2.18 (m, 3H), 2.81-2.88 (m, 1H), 3.71 (t, J=7.3 Hz, 1H), 4.75-4.95 (m, 2H), 7.58 (d, J=8.6 Hz, 2H), 7.84 (d, J=8.6 Hz, 2H), 12.63 (brs, 1H).

Example 5

(−)-2-[4-(Cyclopropylsulfonyl)phenyl]-3-[(1α,3α,4α)-3,4-difluorocyclopentyl]-N-(thiazol-2-yl)propionamide (Compound 1 of the Invention)

[Chemical formula 11]

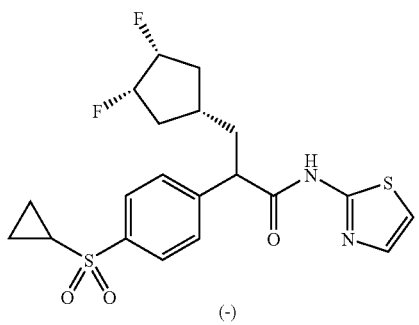

Thionyl chloride (6.1 mL) was added to (−)-2-[4-(Cyclopropylsulfonyl)phenyl]-3-[(1α,3α,4α)-3,4-difluorocyclopentyl]propionic acid (300 mg), and the resulting mixture was heated to reflux for 40 minutes. The mixture was then cooled to room temperature, and the thionyl chloride was removed by distillation. To the resulting mixture toluene (3 mL×2) was added, and then removed by distillation under reduced pressure. Tetrahydrofuran (9.0 mL) was added to the resulting residue, and this mixture was divided into three equal fractions. To one of these fractions (3 mL) a solution of 2-aminothiazole (42.0 mg) in pyridine (1.4 mL) was added over a salt-ice water bath. The resulting mixture was stirred for 15 minutes, followed by stirring for 1 hour at room temperature. To this reaction solution 1 mol/L hydrochloric acid (7 mL) was added, and the mixture was extracted with ethyl acetate (2×7 mL). The organic layer was washed with a saturated aqueous sodium bicarbonate solution (2×10 mL) and saturated brine (10 mL) in that order, dried over anhydrous sodium sulfate, and then filtered. The solvent was removed by distillation under reduced pressure. The resulting residue was purified by silica gel column chromatography (eluant; hexane:ethyl acetate=2:3) to obtain (−)-2-[4-(cyclopropylsulfonyl)phenyl]-3-[(1α,3α,4α)-3,4-difluorocyclopentyl]-N-(thiazol-2-yl)propionamide (84.9 mg).

MS (ESI$^+$) m/z: 441 (ESI$^+$).

HRMS (ESI$^+$) for $C_{20}H_{23}F_2N_2O_3S_2$ (ESI$^+$): calcd., 441.11181; found, 441.11174.

$^1$H NMR (400 MHz, CDCl$_3$) δ 1.00-1.09 (m, 2H), 1.32-1.38 (m, 2H), 1.64-1.89 (m, 3H), 2.00-2.22 (m, 3H), 2.37-2.50 (m, 2H), 3.72 (t, J=7.6 Hz, 1H), 4.70-4.91 (m, 2H), 7.04 (d, J=3.7 Hz, 1H), 7.46 (d, J=3.7 Hz, 1H), 7.49 (d, J=7.9 Hz, 2H), 7.86 (d, J=7.9 Hz, 2H), 10.1 (brs, 1H).

Example 6

Compounds 2 to 66 according to the present invention were produced by the same procedures as in Example 5. The sign of optical rotation in the tables represents the sign of optical rotation as measured with DMF as a solvent for Compounds 7, 13, 14, 36, 48, 50, and 66 of the invention, methanol as a solvent for Compounds 63 and 65 of the invention, and chloroform as a solvent for the remaining Compounds of the invention.

[Chemical formula 12]

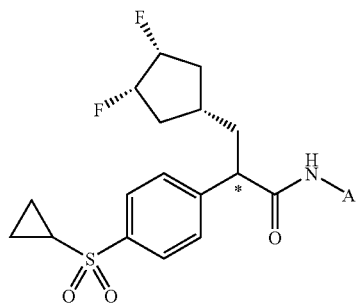

(The Carbon Atoms Marked with an * is in the R-Configuration)

TABLE 1

| No. | Structure (A) | 1H NMR (400 MHz) | MS (m/z) | Sign of Optical Rotation |
|---|---|---|---|---|
| 2 | (pyrazine-methyl) | (CDCl3) δ 1.00-1.09(m, 2H), 1.34-1.40(m, 2H), 1.71-1.91(m, 3H), 2.00-2.23(m, 3H), 2.38-2.50(m, 2H), 3.66(t, J = 7.3 Hz, 1H), 4.72-4.92(m, 2H), 7.57(d, J = 7.9 Hz, 2H), 7.79(s, 1H), 7.91(d, J = 8.6 Hz, 2H), 8.21(t, J = 1.8 Hz, 1H), 8.36(d, J = 3.1 Hz, 1H), 9.52(s, 1H). | (ESI+) 436.2 (MH+) | (−) |
| 3 | (thiazole-methyl-F) | (CDCl3) δ 1.00-1.10(m, 2H), 1.34-1.40(m, 2H), 1.63-1.86(m, 3H), 2.00-2.20(m, 3H), 2.35-2.51(m, 2H), 3.64(t, J = 7.6 Hz, 1H), 4.71-4.94(m, 2H), 7.00(d, J = 3.1 Hz, 1H), 7.51(dd, J = 6.1, 1.8 Hz, 2H), 7.91(dd, J = 8.6, 1.8 Hz, 2H), 8.73(s, 1H). | (ESI+) 459.2 (MH+) | (−) |
| 4 | (pyrazole-methyl-Me) | (DMSO-d6) δ 0.95-1.12(m, 4H), 1.43-1.82(m, 4H), 2.05-2.22(m, 3H), 2.76-2.84(m, 1H), 3.70(s, 3H), 3.84-3.95(m, 1H), 4.76-5.02(m, 2H), 6.39(d, J = 1.8 Hz, 1H), 7.51(d, J = 2.4 Hz, 1H), 7.62(d, J = 7.9 Hz, 2H), 7.84(d, J = 8.6 Hz, 2H), 10.7(s, 1H). | (ESI+) 438.2 (MH+) | (+) |

TABLE 1-continued

| No. | Structure (A) | 1H NMR (400 MHz) | MS (m/z) | Sign of Optical Rotation |
|---|---|---|---|---|
| 5 | 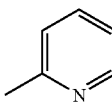 | (DMSO-d6) δ 0.96-1.11(m, 4H), 1.43-1.88(m, 4H), 2.00-2.24(m, 3H), 2.78-2.85(m, 1H), 4.09(t, J = 7.3 Hz, 1H), 4.74-5.00(m, 2H), 7.65(d, J = 8.6 Hz, 2H), 7.85(d, J = 8.6 Hz, 2H), 7.88(dd, J = 8.6, 2.4 Hz, 1H), 8.09(d, J = 8.6 Hz, 1H), 8.36(d, J = 2.4 Hz, 1H), 11.1(s, 1H). | (ESI+) 469.2 (MH+) | (−) |
| 6 | 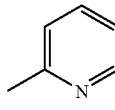 | (DMSO-d6) δ 0.97-1.13(m, 4H), 1.43-1.88(m, 4H), 2.00-2.25(m, 3H), 2.77-2.85(m, 1H), 4.07(t, J = 7.3 Hz, 1H), 4.76-5.03(m, 2H), 7.65(d, J = 8.6 Hz, 2H), 7.71(td, J = 8.6, 3.1 Hz, 1H), 7.85(d, J = 8.6 Hz, 1H), 8.09(dd, J = 9.2, 3.7 Hz, 1H), 8.31(d, J = 3.1 Hz, 1H), 11.0(s, 1H). | (ESI+) 453.2 (MH+) | (−) |

TABLE 2

| No. | Structure (A) | 1H NMR (400 MHz) | MS (m/z) | Sign of Optical Rotation |
|---|---|---|---|---|
| 7 | 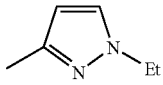 | (DMSO-d6) δ 0.97-1.12(m, 4H), 1.30(t, J = 7.3 Hz, 1H), 1.44-1.82(m, 4H), 2.00-2.22(m, 3H), 2.75-2.85(m, 1H), 3.90(dd, J = 8.3, 6.1 Hz, 1H), 3.98(q, J = 7.3 Hz, 2H), 4.77-5.02(m, 2H), 6.40(d, J = 2.4 Hz, 1H), 7.55(d, J = 2.4 Hz, 1H), 7.62(d, J = 7.9 Hz, 1H), 7.84(d, J = 7.9 Hz, 1H), 10.8(s, 1H). | (ESI+) 452.2 (MH+) | (+) (DMF) |
| 8 | 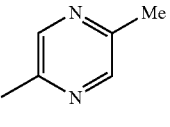 | (DMSO-d6) δ 1.00-1.12(m, 4H), 1.59-1.88(m, 4H), 2.10-2.23(m, 3H), 2.42(s, 3H), 2.79-2.85(m, 1H), 4.09(t, J = 7.3 Hz, 1H), 4.75-5.03(m, 2H), 7.66(d, J = 8.6 Hz, 2H), 7.86(d, J = 8.6 Hz, 1H), 8.27(d, J = 1.2 Hz, 1H), 9.17(d, J = 1.2 Hz, 1H), 11.0(s, 1H). | (ESI+) 450.2 (MH+) | (−) |
| 9 | 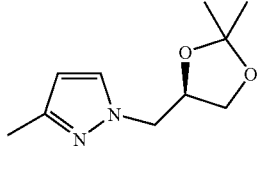 | (DMSO-d6) δ 0.96-1.12(m, 4H), 1.23(s, 3H), 1.29(s, 3H), 1.41-1.82(m, 4H), 2.00-2.24(m, 3H), 2.77-2.84(m, 1H), 3.69(dd, J = 8.6, 5.5 Hz, 1H), 3.91(dd, J = 8.6, 6.1 Hz, 1H), 3.97(dd, J = 8.6, 6.1 Hz, 1H), 4.07(m, 2H), 4.32(ddd, J = 17.1, 6.1, 5.5 Hz, 1H), 4.78-5.01(m, 2H), 6.43(d, J = 2.4 Hz, 1H), 7.57(d, J = 2.4 Hz, 1H), 7.63(d, J = 8.6 Hz, 2H), 7.84(d, J = 8.6 Hz, 2H), 10.8(s, 1H). | (ESI+) 538.2 (MH+) | (−) |
| 10 | 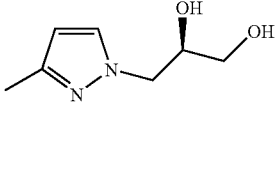 | (DMSO-d6) δ 0.97-1.12(m, 4H), 1.42-1.83(m, 4H), 2.01-2.23(m, 3H), 2.75-2.84(m, 1H), 3.20-3.38(m, 2H), 3.71-3.79(m, 1H), 3.82(d, J = 13.5 Hz, 1H), 3.85(d, J = 14.1 Hz, 1H), 3.90(dd, J = 8.6, 6.7 Hz, 1H), 4.04(dd, J = 4.0, 14.1 Hz, 1H), 4.68(t, J = 6.1 Hz, 1H), 4.78-5.01(m, 2H), 4.90(d, J = 4.9 Hz, 1H), 6.40(d, J = 2.4 Hz, 1H), 7.49(d, J = 2.4 Hz, 1H), 7.62(d, J = 8.6 Hz, 2H), 7.84(d, J = 8.6 Hz, 2H), 10.8(s, 1H). | (ESI+) 498.2 (MH+) | (−) |

TABLE 3

| No. | Structure (A) | 1H NMR (400 MHz) | MS (m/z) | Sign of Optical Rotation |
|---|---|---|---|---|
| 11 | 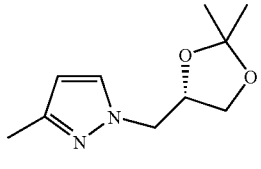 | (DMSO-d6) δ 0.98-1.12(m, 4H), 1.22(s, 3H), 1.29(s, 3H), 1.40-1.85(m, 4H), 2.00-2.26(m, 3H), 2.75-2.85(m, 1H), 3.70(dd, J = 8.6, 5.5 Hz, 1H), 3.91(dd, J = 8.6, 6.1 Hz, 1H), 3.98(dd, J = 8.6, 6.1 Hz, 1H), 4.07(m, 2H), 4.31(ddd, J = 17.1, 6.1, 5.5 Hz, 1H), 4.75-5.02(m, 2H), 6.43(d, J = 2.4 Hz, 1H), 7.57(d, J = 2.4 Hz, 1H), 7.62(d, J = 8.6 Hz, 2H), 7.84(d, J = 8.6 Hz, 2H), 10.8(s, 1H). | (ESI+) 538.2 (MH+) | (−) |

TABLE 3-continued

| No. | Structure (A) | 1H NMR (400 MHz) | MS (m/z) | Sign of Optical Rotation |
|---|---|---|---|---|
| 12 | *(pyrazole with CH2-CH(OH)-CH2OH substituent)* | (DMSO-d6) δ 0.97-1.11(m, 4H), 1.43-1.84(m, 4H), 1.99-2.25(m, 3H), 2.75-2.84(m, 1H), 3.20-3.38(m, 2H), 3.67-3.77(m, 1H), 3.80(d, J = 13.5 Hz, 1H), 3.84(d, J = 14.1 Hz, H), 3.89(dd, J = 8.6, 6.7 Hz, 1H), 4.03(dd, J = 14.1, 4.0 Hz, 1H), 4.68(t, J = 6.1 Hz, 1H), 4.77-5.02(m, 2H), 4.89(d, J = 4.9 Hz, 1H), 6.40(d, J = 2.4 Hz, 1H), 7.49(d, J = 2.4 Hz, 1H), 7.62(d, J = 8.6 Hz, 2H), 7.83(d, J = 8.6 Hz, 2H), 10.8(s, 1H). | (ESI+) 498.2 (MH+) | (−) |
| 13 | *(pyrazole with CHF2 substituent)* | (DMSO-d6) δ 0.98-1.14(m, 4H), 1.46-1.84(m, 4H), 2.03-2.22(m, 3H), 2.78-2.84(m, 1H), 3.92(t, J = 7.6 Hz, 1H), 4.79-5.00(m, 2H), 6.73(d, J = 3.1 Hz, 1H), 7.63(d, J = 8.6 Hz, 2H), 7.66(t, J = 58.7 Hz, 1H), 7.85(d, J = 8.6 Hz, 2H), 8.07(d, J = 3.1 Hz, 1H), 11.2(br, 1H). | (ESI+) 474.2 (MH+) | (+) (DMF) |
| 14 | *(pyrazole with CH2CF3 substituent)* | (DMSO-d6) δ 0.98-1.11(m, 4H), 1.45-1.82(m, 4H), 2.00-2.21(m, 3H), 2.78-2.84(m, 1H), 3.91(t, J = 7.6 Hz, 1H), 4.79-5.02(m, 4H), 6.57(d, J = 2.4 Hz, 1H), 7.62(d, J = 8.6 Hz, 2H), 7.70-(d, J = 2.4 Hz, 1H), 7.84(d, J = 8.6 Hz, 2H), 11.0(br, 1H). | (ESI+) 506.2 (MH+) | (+) (DMF) |

TABLE 4

| No. | Structure (A) | 1H NMR (400 MHz) | MS (m/z) | Sign of Optical Rotation |
|---|---|---|---|---|
| 15 | *(2-methylthiazolo[5,4-b]pyridine-OCH2CH2OMe)* | (DMSO-d6) δ 0.94-1.11 (m, 4H), 1.44-1.81 (m, 3H), 1.81-1.98 (m, 1H), 2.01-2.29 (m, 3H), 2.77-2.86 (m, 1H), 3.31 (s, 3H), 3.66 (t, J = 4.3 Hz, 2H), 3.96-4.12 (m, 1H), 4.39 (t, J = 4.3 Hz, 2H), 4.75-5.03 (m, 2H), 6.89 (d, J =0 8.6 Hz, 1H), 7.66 (d, J = 8.6 Hz, 2H), 7.87 (d, J = 8.6 Hz, 2H), 7.92-8.05 (m, 1H), 12.7 (br, 1H). | (ESI+) 566.2 (MH+) | (−) |
| 16 | *(6-methylpyridin-3-yl cyclopropyl)* | (CDCl3) δ 0.62-0.68 (m, 2H), 0.96-1.07 (m, 4H), 1.33-1.38 (m, 2H), 1.63-1.90 (m, 4H), 1.96-2.06 (m, 1H), 2.06-2.22 (m, 2H), 2.35-2.49 (m, 2H), 3.57 (t, J = 7.6 Hz, 1H), 4.69-4.93 (m, 2H), 7.30-7.35 (m, 2H), 7.54 (d, J = 7.9 Hz, 2H), 7.84-7.90 (m, 3H), 8.02-8.08 (m, 2H). | (ESI+) 475.2 (MH+) | (−) |
| 17 | *(6-methylpyridin-3-yl SEt)* | (CDCl3) δ 1.01-1.07 (m, 2H), 1.26 (t, J = 7.3 Hz, 3H), 1.33-1.39 (m, 2H), 1.64-1.91 (m, 3H), 1.91-2.22 (m, 3H), 2.35-2.49 (m, 2H), 2.87 (q, J = 7.3 Hz, 2H), 3.59 (t, J = 7.9 Hz, 1H), 4.70-4.94 (m, 2H), 7.54 (d, J = 7.9 Hz, 2H), 7.71 (dd, J = 8.6, 2.4 Hz, 1H), 7.85-7.92 (m, 3H), 8.13 (d, J = 8.6 Hz, 1H), 8.22 (d, J = 2.4 Hz, 1H). | (ESI+) 495.2 (MH+) | (−) |
| 18 | *(5-methylpyrazin-2-yl SMe)* | (DMSO-d6) δ 0.93-1.10 (m, 4H), 1.40-1.88 (m, 4H), 1.97-2.21 (m, 3H), 2.73-2.81 (m, 1H), 4.06 (t, J = 7.3 Hz, 1H), 4.74-5.00 (m, 2H), 7.63 (d, J = 8.6 Hz, 2H), 7.82 (d, J = 8.6 Hz, 2H), 8.31 (d, J = 1.8 Hz, 1H), 9.12 (d, J = 1.8 Hz, 1H), 11.0 (s, 1H). | (ESI+) 482.1 (MH+) | (−) |
| 19 | *(5-methylpyrazin-2-yl OCH2CH2OMe)* | (DMSO-d6) δ 0.94-1.14 (m, 4H), 1.44-1.90 (m, 4H), 1.98-2.26 (m, 3H), 2.76-2.87 (m, 1H), 3.27 (s, 3H), 3.64 (t, J = 4.9 Hz, 1H), 4.07 (t, J = 7.3 Hz, 1H), 4.36 (dd, J = 4.9, 6.1 Hz, 1H), 4.76-5.02 (m, 2H), 7.66 (d, J = 8.6 Hz, 2H), 7.86 (d, J = 8.6 Hz, 2H), 8.09 (d, J = 1.8 Hz, 1H), 8.82 (d, J = 1.8 Hz, 1H), 10.9 (s, 1H). | (ESI+) 510.2 (MH+) | (−) |

TABLE 5

| No. | Structure (A) | 1H NMR (400 MHz) | MS (m/z) | Sign of Optical Rotation |
|---|---|---|---|---|
| 20 | (pyrazine with methyl and isopropoxy) | (CDCl3) δ 1.01-1.07 (m, 2H), 1.32-1.39 (m, 8H), 1.64-1.91 (m, 3H), 1.96-2.23 (m, 3H), 2.35-2.50 (m, 2H), 3.61 (t, J = 7.6 Hz, 1H), 4.71-4.93 (m, 2H), 5.24 (m, 1H), 7.56 (d, J = 8.6 Hz, 2H), 7.61 (s, 1H), 7.79 (d, J = 1.8 Hz, 1H), 7.90 (d, J = 8.6 Hz, 2H), 8.96 (s, 1H). | (ESI+) 494.2 (MH+) | (−) |
| 21 | (pyrazine with methyl and Et) | (DMDO-d6) δ 0.96-1.14 (m, 4H), 1.19 (t, J = 7.3 Hz, 3H), 1.44-1.90 (m, 4H), 1.99-2.25 (m, 3H), 2.72 (q, J = 7.3 Hz, 2H), 2.75-2.86 (m, 1H), 4.09 (t, J = 7.3 Hz, 1H), 4.74-5.04 (m, 2H), 7.66 (d, J = 8.6 Hz, 2H), 7.86 (d, J = 8.6 Hz, 2H), 8.28 (d, J = 1.8 Hz, 1H), 9.19 (d, J = 1.8 Hz, 1H), 11.1 (s, 1H). | (ESI+) 464.2 (MH+) | (−) |
| 22 | (pyrazine with methyl and OCH2CH2SMe) | (DMSO-d6) δ 0.95-1.14 (m, 4H), 1.42-1.90 (m, 4H), 1.99-2.25 (m, 3H), 2.11 (s, 3H), 2.76-2.87 (m, 3H), 4.07 (t, J = 7.3 Hz, 1H), 4.41 (t, J − 6.7 Hz, 1H), 4.15-5.02 (m, 2H), 7.66 (d, J = 8.6 = Hz, 2H), 7.86 (d, J = 8.6 Hz, 2H), 8.09 (d, J = 1.8 Hz, 1H), 8.83 (d, J = 1.8 Hz, 1H), 10.9 (s, 1H). | (ESI+) 526.2 (MH+) | (−) |
| 23 | (pyrazine with methyl and OMe) | (DMSO-d6) δ 0.94-1.13 (m, 4H), 1.43-1.92 (m, 4H), 2.01-2.25 (m, 3H), 2.75-2.81 (m, 1H), 4.07 (t, J = 7.3 Hz, 1H), 4.71-5.04 (m, 2H), 7.66 (d, J = 8.6 Hz, 2H), 7.86 (d, J = 8.6 Hz, 2H), 8.09 (d, J = 1.8 Hz, 1H), 8.84 (d, J = 1.8 Hz, 1H), 10.9 (s, 1H). | (ESI+) 466.2 (MH+) | (−) |
| 24 | (pyrazole with methyl and CH2C(CH3)2OH) | (DMSO-d6) δ 1.45 (s, 3H), 1.48 (s, 3H), 1.62-1.87 (m, 3H), 1.99-2.21 (m, 3H), 2.33-2.47 (m, 1H), 3.07 (s, 3H), 3.66 (t, J = 7.3 Hz, 1H), 3.93 (dd, J = 1.2 7.3 Hz, 1H), 4.26 (dd, J = 1.2, 7.3 Hz, 1H), 4.70-4.93 (m, 2H), 5.08 (t, J = 7.3 Hz, 1H), 6.93 (s, 1H), 7.48 (d, J = 8.6 Hz, 1H), 7.93 (d, J = 8.6 Hz, 1H), 8.80 (s, 1H). | (ESI+) 515.2 (MH+) | (−) |

TABLE 6

| No. | Structure (A) | 1H NMR (400 MHz) | MS (m/z) | Sign of Optical Rotation |
|---|---|---|---|---|
| 25 | (2-methylbenzothiazole with morpholine) | (CDCl3) δ 1.01-1.11 (m, 2H), 1.33-1.39 (m, 2H), 1.51-1.82 (m, 3H), 1.89-2.19 (m, 3H), 2.28-2.39 (m, 1H), 2.41-2.50 (m, 1H), 3.23 (t, J = 4.9 Hz, 4H), 3.56 (t, J = 7.6 Hz, 1H), 3.91 (t, J = 4.9 Hz, 4H), 4.66-4.92 (m, 2H), 7.06 (d, J = 7.9 Hz, 2H), 7.14 (dd, J = 9.2, 2.4 Hz, 1H), 7.32 (d, J = 2.4 Hz, 1H), 7.66 (d, J = 8.6 Hz, 1H), 7.71 (d, J = 8.6 Hz, 2H). | (ESI+) 576.2 (MH+) | (−) |
| 26 | (2-methylbenzothiazole with isopropyl ester) | (CDCl3) δ 1.04-1.11 (m, 2H), 1.35-1.44 (m, 8H), 1.63-1.89 (m, 3H), 1.99-2.20 (m, 3H), 2.37-2.54 (m, 2H), 3.70 (t, J = 7.6 Hz, 1H), 4.69-4.95 (m, 2H), 5.29 (m, 1H), 7.40 (d, J = 7.9 Hz, 2H), 7.75 (d, J = 8.6 Hz, 1H), 7.87 (d, J = 7.9 Hz, 2H), 8.14 (dd, J = 8.6, 1.8 Hz, 1H), 8.55 (d, J = 1.8 Hz, 1H), 9.33 (s, 1H). | (ESI+) 577.2 (MH+) | (−) |
| 27 | (2-methylbenzothiazole with OCH2CH2OMe ester) | (CDCl3) δ 1.01-1.12 (m, 2H), 1.33-1.43 (m, 2H), 1.64-1.88 (m, 3H), 1.98-2.19 (m, 3H), 2.36-2.52 (m, 2H), 3.45 (s, 3H), 3.70 (t, J = 7.9 Hz, 1H), 3.75-3.79 (m, 2H), 4.49-4.55 (m, 2H), 4.69-4.77 (m, 2H), 7.32-7.40 (m, 2H), 7.75 (d, J = 8.6 Hz, 1H), 7.81-7.88 (m, 2H), 8.16 (dd, J = 8.6, 1.8 Hz, 1H), 8.58 (d, J = 1.8 Hz, 1H), 9.67 (br, 1H). | (ESI+) 593.2 (MH+) | (−) |
| 28 | (2-methylthiazolopyridine) | (DMSO-d6) δ 0.94-1.15 (m, 4H), 1.42-1.81 (m, 3H), 1.82-2.00 (m, 1H), 2.00-2.29 (m, 3H), 2.77-2.88 (m, 1H), 4.10 (t, J = 7.3 Hz, 1H), 4.71-5.04 (m, 2H), 7.47 (dd, J = 4.9, 8.6 Hz, 1H), 7.67 (d, J = 8.6 Hz, 2H), 7.88 (d, J = 8.6 Hz, 2H), 8.09 (d, J = 8.6 Hz, 1H), 8.45 (d, J = 4.9 Hz, 1H), 12.9 (s, 1H). | (ESI+) 492.1 (MH+) | (−) |

TABLE 7

| No. | Structure (A) | 1H NMR (400 MHz) | MS (m/z) | Sign of Optical Rotation |
|---|---|---|---|---|
| 29 | 2-methylthiazol-4-yl attached to dioxolane (with *) | (DMSO-d6) δ 1.00-1.13 (m, 4H), 1.34 (s, 3H), 1.37 (s, 3H), 1.45-1.80 (m, 3H), 1.80-1.92 (m, 1H), 2.00-2.27 (m, 3H), 2.19-2.86 (m, 1H), 3.84 (t, J = 7.3 Hz, 1H), 4.01 (t, J = 7.3 Hz, 1H), 4.21 (dd, J = 6.7, 7.9 Hz, 1H), 4.77-5.00 (m, 2H), 5.05 (t, J = 6.7 Hz, 1H), 7.10 (s, 1H), 7.63 (d, J = 8.6 Hz, 2H), 7.86 (d, J = 8.6 Hz, 2H), 12.5 (s, 1H). | (ESI+) 541.2 (MH+) | (−) |
| 30 | 2-methyl-4-Me-thiazole | (DMSO-d6) δ 0.92-1.14 (m, 4H), 1.42-1.76 (m, 3H), 1.76-1.92 (m, 1H), 2.00-2.25 (m, 3H), 2.23 (s, 3H), 2.76-2.86 (m, 1H), 3.99 (t, J = 7.3 Hz, 1H), 4.72-5.05 (m, 2H), 6.75 (s, 1H), 7.63 (d, J = 8.6 Hz, 2H), 7.86 (d, J = 8.6 Hz, 2H), 12.4 (s, 1H). | (ESI+) 455.1 (MH+) | (−) |
| 31 | 2-methyl-5-Me-thiazole | (DMSO-d6) δ 0.94-1.14 (m, 4H), 1.44-1.78 (m, 3H), 1.78-1.93 (m, 1H), 1.99-2.25 (m, 3H), 2.30 (d, J = 1.2 Hz, 3H), 2.77-2.86 (m, 1H), 4.00 (t, J = 7.3 Hz, 1H), 4.75-5.02 (m, 2H), 7.12 (d, J = 1.2 Hz, 1H), 7.63 (d, J = 8.6 Hz, 2H), 7.86 (d, J = 8.6 Hz, 2H), 12.3 (s, 1H). | (ESI+) 455.1 (MH+) | (−) |
| 32 | 2-methyl-4-tBu-thiazole | (CDCl3) δ 1.01-1.09 (m, 2H), 1.26 (s, 9H), 1.33-1.42 (m, 2H), 1.60-1.90 (m, 3H), 1.96-2.20 (m, 3H), 2.36-2.53 (m, 2H), 3.64 (t, J = 7.9 Hz, 1H), 4.68-4.93 (m, 2H), 6.55 (s, 1H), 7.47-7.54 (m, 2H), 7.85-7.92 (m, 2H), 8.71-8.91 (m, 1H). | (ESI+) 497.2 (MH+) | (−) |
| 33 | 2-methyl-5-Br-thiazole | (CDCl3) δ 1.01-1.01 (m, 2H), 1.33-1.38 (m, 2H), 1.63-1.86 (m, 3H), 2.00-2.18 (m, 3H), 2.36-2.48 (m, 2H), 3.66 (t, J = 7.7 Hz, 1H), 4.71-4.90 (m, 2H), 7.32 (s, 1H), 7.46 (d, J = 8 Hz, 2H), 7.87 (d, J = 8 Hz, 2H), 9.38 (s, 1H). | (ESI+) 519.0 (MH+) | (−) |

TABLE 8

| No. | Structure (A) | 1H NMR (400 MHz) | MS (m/z) | Sign of Optical Rotation |
|---|---|---|---|---|
| 34 | methyl-thiadiazole | (DMSO-d6) δ 0.98-1.09 (m, 4H), 1.45-1.75 (m, 3H), 1.89-2.30 (m, 4H), 2.79-2.86 (m, 1H), 4.11 (t, J = 7.3 Hz, 1H), 4.77-5.00 (m, 2H), 7.63 (d, J = 8.6 Hz, 2H), 7.88 (d, J = 8.6 Hz, 2H), 8.47 (s, 1H), 13.3 (s, 1H). | (ESI+) 442.1 (MH+) | (−) |
| 35 | methyl-Et-thiadiazole | (CDCl3) δ 1.03-1.13 (m, 2H), 1.31 (t, J = 7.3 Hz, 3H), 1.37-1.44 (m, 2H), 1.63-1.89 (m, 3H), 1.99-2.22 (m, 3H), 2.38-2.53 (m, 2H), 2.83 (q, J = 7.3 Hz, 2H), 3.77 (t, J = 7.9 Hz, 1H), 4.69-4.93 (m, 2H), 7.48 (d, J = 7.9 Hz, 2H), 7.90 (d, J = 8.6 Hz, 2H), 9.25 (s, 1H). | (ESI+) 470.1 (MH+) | (−) |
| 36 | methyl-morpholino-thiadiazole | (CDCl3) δ 1.03-1.11 (m, 2H), 1.33-1.43 (m, 2H), 1.64-1.90 (m, 3H), 1.98-2.22 (m, 3H), 2.35-2.52 (m, 2H), 3.55 (t, J = 5.5 Hz, 4H), 3.70-3.78 (m, 5H), 4.70-4.94 (m, 2H), 7.44-7.52 (m, 2H), 7.84-7.93 (m, 2H), 9.24 (br, 1H). | (ESI+) 527.2 (MH+) | (+) (DMF) |
| 37 | methyl-pyridyl-S-C(Me)2-CO2Et | (CDCl3) δ 1.01-1.08 (m, 2H), 1.24 (t, J = 7.1 Hz, 3H), 1.33-1.39 (m, 2H), 1.46 (s, 6H), 1.64-1.91 (3H, m), 1.96-2.23 (m, 3H), 2.35-2.51 (m, 2H), 3.60 (t, J = 7.6 Hz, 1H), 4.12 (q, J = 7.1 Hz, 2H), 4.70-4.94 (m, 2H), 7.54 (d, J = 8.6 Hz, 2H), 7.78 (dd, J = 8.6, 1.8 Hz, 1H), 7.88-7.92 (m, 3H), 8.17 (d, J = 9.2 Hz, 1H), 8.25 (d, J = 2.4 Hz, 1H). | (ESI+) 581.2 (MH+) | (−) |

TABLE 8-continued

| No. | Structure (A) | 1H NMR (400 MHz) | MS (m/z) | Sign of Optical Rotation |
|---|---|---|---|---|
| 38 | (pyrazine-methyl substituted, linked via O-CH2CH2-O-tetrahydropyran) | (CDCl3) δ 0.99-1.08 (m, 2H), 1.31-1.40 (m, 2H), 1.45-1.91 (m, 9H), 1.98-2.24 (m, 3H), 2.35-2.51 (m, 2H), 3.49-3.55 (m, 1H), 3.61 (t, J = 7.6 Hz, 1H), 3.75-3.83 (m, 1H), 3.84-3.92 (m, 1H), 4.01-4.08 (m, 1H), 4.43-4.55 (m, 2H), 4.67 (s, 1H), 4.71-4.93 (m, 2H), 7.56 (d, J = 7.9 Hz, 2H), 7.63 (s, 1H), 7.88-7.92 (m, 3H), 8.97 (s, 1H). | (ESI+) 580.2 (MH+) | (−) |

TABLE 9

| No. | Structure (A) | 1H NMR (400 MHz) | MS (m/z) | Sign of Optical Rotation |
|---|---|---|---|---|
| 39 | (methylpyrazine-O-CH2CH2-OH) | (CDCl3) δ 1.01-1.08 (m, 2H), 1.32-1.39 (m, 2H), 1.65-1.89 (m, 3H), 1.99-2.23 (m, 3H), 2.30-2.50 (m, 3H), 3.62 (t, J = 7.6 Hz, 1 H), 3.94-4.00 (m, 2H), 4.42-4.49 (m, 2H), 4.71-4.94 (m, 2H), 7.52-7.59 (m, 2H), 7.67 (s, 1H), 7.88-7.93 (m, 3H), 8.98 (s, 1H). | (ESI+) 496.2 (MH+) | (−) |
| 40 | (methylpyrazine-O-CH2CH2CH2-OMe) | (CDCl3) δ 1.01-1.08 (m, 2H), 1.33-1.39 (m, 2H), 1.64-1.91 (m, 3H), 1.97-2.22 (m, 5H), 2.36-2.50 (m, 2H), 3.34 (s, 3H), 3.52 (t, J = 6.1 Hz, 2H), 3.62 (t, J = 7.9 Hz, 1H), 4.39 (t, J = 6.1 Hz, 2H), 4.70-4.93 (m, 2H), 7.56 (d, J = 8.6 Hz, 2H), 7.62-7.68 (m, 1H), 7.85 (d, J = 1.2 Hz, 1H), 7.90 (d, J = 8.6 Hz, 2H), 8.97 (s, 1H). | (ESI+) 524.2 (MH+) | (−) |
| 41 | (methylpyrazine-O-CH2CH2-OEt) | (CDCl3) δ 1.01-1.08 (m, 2H), 1.23 (t, J = 7.3 Hz, 3H), 1.33-1.40 (m, 2H), 1.65-1.91 (m, 3H), 1.98-2.23 (m, 3H), 2.35-2.50 (m, 2H), 3.58 (q, J = 7.3 Hz, 2H), 3.62 (t, J = 7.3 Hz, 1H), 3.75-3.80 (m, 2H), 4.43-4.49 (m, 2H), 4.70-4.93 (m, 2H), 7.56 (d, J = 8.6 Hz, 2H), 7.63-7.73 (m, 1H), 7.89 (d, J = 7.9 Hz, 2H), 7.92 (d, J = 1.2 Hz, 1H), 8.97 (s, 1H). | (ESI+) 524.2 (MH+) | (−) |
| 42 | (methylpyrazine-dioxolane-dimethyl) | (CDCl3) δ 1.02-1.08 (m, 2H), 1.34-1.39 (m, 2H), 1.48 (s, 3H), 1.51 (s, 3H), 1.67-1.89 (m, 3H), 2.02-2.22 (m, 3H), 2.37-2.49 (m, 2H), 3.65 (t, J = 7.6 Hz, 1H), 3.97 (dd, J = 8.6, 6.7 Hz, 1H), 4.43 (dd, J = 8.6, 6.7 Hz, 1H), 4.93-4.73 (m, 2H), 5.21 (t, J = 6.4 Hz, 1H), 7.55 (d, J = 8.6 Hz, 2H), 7.78 (s, 1H), 7.91 (d, J = 8.6 Hz, 2H), 8.41 (d, J = 1.2 Hz, 1H), 9.42 (d, J = 1.2 Hz, 1H). | (ESI+) 536.2 (MH+) | (−) |
| 43 | (methylpyrazine-CH(OH)-CH2OH) | (CDCl3) δ 1.02-1.08 (m, 2H), 1.35-1.39 (m, 2H), 1.67-1.88 (m, 3H), 2.02-2.22 (m, 3H), 2.36-2.48 (m, 3H), 3.51-3.61 (m, 1H), 3.64-3.74 (m, 1H), 3.81-3.87 (m, 1H), 3.92-3.99 (m, 1H), 4.72-4.93 (m, 3H), 7.55 (d, J = 8.6 Hz, 2H), 7.90 (d, J = 8.6 Hz, 2H), 8.02 (s, 1H), 8.34 (s, 1H), 9.43 (s, 1H). | (ESI+) 496.2 (MH+) | (−) |

TABLE 10

| No. | Structure (A) | 1H NMR (400 MHz) | MS (m/z) | Sign of Optical Rotation |
|---|---|---|---|---|
| 44 | (methylpyrazine-dioxolane-dimethyl, stereo) | (CDCl3) δ 1.02-1.07 (m, 2H), 1.34-1.39 (m, 2H), 1.48 (s, 3H), 1.52 (s, 3H), 1.66-1.90 (m, 3H), 2.02-2.22 (m, 3H), 2.31-2.49 (m, 2H), 3.65 (t, J = 7.3 Hz, 1H), 4.00 (dd, J = 8.3, 6.4 Hz, 1H), 4.44 (dd, J = 8.3, 6.4 Hz, 1H), 4.93-4.12 (m, 2H), 5.20 (t, J = 6.4 Hz, 1H), 7.56 (d, J = 8.6 Hz, 2H), 7.79 (s, 1H), 7.91 (d, J = 8.6 Hz, 2H), 8.40 (d, J = 1.2 Hz, 1H), 9.42 (d, J = 1.2 Hz, 1H). | (ESI+) 536.2 (MH+) | (−) |

TABLE 10-continued

| No. | Structure (A) | 1H NMR (400 MHz) | MS (m/z) | Sign of Optical Rotation |
|---|---|---|---|---|
| 45 | (5-methylpyrazin-2-yl with CH(OH)CH2OH) | (CDCl3) δ 1.02-1.08 (m, 2H), 1.35-1.39 (m, 2H), 1.67-1.88 (m, 3H), 2.02-2.21 (m, 3H), 2.38-2.49 (m, 3H), 3.58 (d, J = 4.9 Hz, 1H), 3.68 (t, J = 7.6 Hz, 1H), 3.80-3.86 (m, 1H), 3.91-3.98 (m, 1H), 4.72-4.93 (m, 3H), 7.55 (d, J = 8.6 Hz, 2H), 7.90 (d, J = 8.6 Hz, 2H), 8.00 (s, 1H), 8.34 (s, 1H), 9.43 (s, 1H). | (ESI+) 496.2 (MH+) | (−) |
| 46 | (5-methylpyrazin-2-yl-S-CH2CH2OH) | (CDCl3) δ 1.02-1.08 (m, 2H), 1.34-1.39 (m, 2H), 1.67-1.87 (m, 3H), 2.01-2.20 (m, 3H), 2.31-2.49 (m, 2H), 3.11 (s, 1H), 3.34 (t, J = 5.5 Hz, 2H), 3.65 (t, J = 7.3 Hz, 1H), 3.90 (t, J = 5.5 Hz, 2H), 4.72-4.92 (m, 3H), 7.55 (d, J = 8.6 Hz, 2H), 7.82 (s, 1H), 7.90 (d, J = 8.6 Hz, 2H), 8.17 (d, J = 1.2 Hz, 1H), 9.30 (d, J = 1.2 Hz, 1H). | (ESI+) 512.2 (MH+) | (−) |
| 47 | (3,5,6-trimethylpyrazin-2-yl) | (CDCl3) δ 1.05 (ddd, J = 14.1, 7.9, 1.8 Hz, 2H), 1.34-1.39 (m, 2H), 1.65-1.83 (m, 2H), 1.80-1.93 (m, 1H), 1.98-2.07 (m, 1H), 2.09-2.23 (m, 2H), 2.35 (s, 3H), 2.37-2.50 (m, 2H), 2.52 (s, 3H), 3.78 (br, 1H), 4.73-4.93 (m, 2H), 7.34 (br, 1H), 7.56 (d, J = 8.0 Hz, 1H), 7.89 (d, J = 8.0 Hz, 2H), 8.06 (s, 1H). | (ESI+) 464.2 (MH+) | (−) |

TABLE 11

| No. | Structure (A) | 1H NMR (400 MHz) | MS (m/z) | Sign of Optical Rotation |
|---|---|---|---|---|
| 48 | (3-methylpyrazol-1-yl-CH2CH2F) | (DMSO-d6) δ 0.97-1.40 (m, 2H), 1.05-1.12 (m, 2H), 1.45-1.68 (m, 2H), 1.61-1.81 (2H, m), 2.02-2.22 (m, 3H), 2.76-2.84 (m, 1H), 3.90 (dd, J = 8.6, 6.1 Hz, 1H), 4.28 (dt, J = 27.5, 4.9 Hz, 2H), 4.68 (dt, J = 47.7, 4.3 Hz, 2H), 4.78-5.00 (m, 2H), 6.45 (d, J = 2.5 Hz, 1H), 7.60 (d, J = 2.8 Hz, 1H), 7.62 (d, J = 8.0 Hz, 2H), 7.83 (d, J = 8.0 Hz, 2H), 10.8 (s, 1H). | (ESI+) 470.2 (MH+) | (+) (DMF) |
| 49 | (3-methylpyrazol-1-yl-CH(Me)2) | (CDCl3) δ 1.04 (ddd, J = 13.5, 8.0, 2.4 Hz, 1H), 1.33-1.39 (m, 2H), 1.43 (d, J = 6.1 Hz, 6H), 1.65-1.80 (m, 2H), 1.80-1.91 (m, 1H), 1.94-2.03 (m, 1H), 2.07-2.21 (m, 2H), 2.37-2.48 (m, 2H), 3.53 (t, J = 8.0 Hz, 1H), 4.31 (m, 1H), 4.70-4.91 (m, 2H), 6.63 (d, J = 1.8 Hz, 1H), 7.30 (d, J = 2.5 Hz, 1H), 7.54 (d, J = 8.6 Hz, 2H), 7.72 (br, 1H), 7.87 (d, J = 8.6 Hz, 2H). | (ESI+) 466.2 (MH+) | (−) |
| 50 | (3-methylpyrazol-1-yl-CH2CH2OH) | (DMSO-d6) δ 0.97-1.40 (m, 2H), 1.05-1.12 (m, 2H), 1.45-1.68 (m, 2H), 1.67-1.81 (2H, m), 2.02-2.22 (m, 3H), 2.76-2.84 (m, 1H), 3.66 (q, J = 5.5 Hz, 2H), 3.90 (dd, J = 8.6, 6.7 Hz, 1H), 3.98 (t, J = 6.1 Hz, 2H), 4.81 (t, J = 5.5 Hz, 1H), 4.80-5.00 (m, 2H), 6.40 (d, J = 2.5 Hz, 1H), 7.52 (d, J = 1.8 Hz, 1H), 7.62 (d, J = 8.6 Hz, 2H), 7.84 (d, J = 8.6 Hz, 2H), 10.8 (br, 1H). | (ESI+) 468.2 (MH+) | (+) (DMF) |
| 51 | (3-methylisoxazol-5-yl) | (DMSO-d6) δ 0.96-1.13 (m, 4H), 1.40-1.90 (m, 4H), 2.00-2.24 (m, 3H), 2.77-2.86 (m, 1H), 3.96 (t, J = 7.3 Hz, 1H), 4.73-5.02 (m, 2H), 6.90 (d, J = 1.8 Hz, 1H), 7.63 (d, J = 8.6 Hz, 2H), 7.86 (d, J = 8.6 Hz, 2H), 8.78 (d, J = 1.8 Hz, 1H), 11.4 (s, 1H). | (ESI+) 425.1 (MH+) | (−) |

TABLE 12

| No. | Structure (A) | 1H NMR (400 MHz) | MS (m/z) | Sign of Optical Rotation |
|---|---|---|---|---|
| 52 | (2-methylbenzothiazole with OMe) | (CDCl3) δ 1.04-1.10 (m, 2H), 1.34-1.39 (m, 2H), 1.54-1.81 (m, 3H), 1.94-2.14 (m, 3H), 2.33-2.40 (m, 1H), 2.43-2.50 (m, 1H), 3.59 (t, J = 7.6 Hz, 1H), 3.89 (s, 3H), 4.70-4.91 (m, 2H), 7.08 (dd, J = 8.6, 2.4 Hz, 1H), 7.18 (d, J = 8.6 Hz, 2H), 7.32 (d, J = 2.4 Hz, 1H), 7.65 (d, J = 8.6 Hz, 1H), 7.76 (d, J = 8.6 Hz, 2H), 9.88 (s, 1H). | (ESI+) 521.1 (MH+) | (−) |
| 53 | (2-methylbenzothiazole) | (CDCl3) δ 1.04-1.10 (m, 2H), 1.35-1.39 (m, 2H), 1.54-1.81 (m, 3H), 1.93-2.18 (m, 3H), 2.33-2.40 (m, 1H), 2.43-2.50 (m, 1H), 3.61 (t, J = 7.3 Hz, 1H), 4.69-4.92 (m, 2H), 1.13 (d, J = 7.9 Hz, 2H), 7.38 (t, J = 7.6 Hz, 1H), 7.48-7.52 (m, 1H), 7.74-7.79 (m, 3H), 7.87 (d, J = 7.9 Hz, 1H), 10.0 (s, 1H). | (ESI+) 491.1 (MH+) | (−) |
| 54 | (2-methylbenzothiazole with OCHF2) | (DMSO-d6) δ 0.91-1.12 (m, 4H), 1.41-1.76 (m, 3H), 1.85-1.99 (m, 1H), 1.99-2.28 (m, 3H), 2.75-2.85 (m, 1H), 4.06 (t, J = 7.3 Hz, 1H), 4.41 (t, J = 6.7 Hz, 1H), 4.73-5.00 (m, 2H), 7.22 (t, J = 74.0 Hz, 1H), 7.23 (dd, J = 2.4, 8.6 Hz, 1H), 7.65 (d, J = 8.6 Hz, 2H), 7.73 (d, J = 8.6 Hz, 1H), 7.85 (d, J = 2.4 Hz, 1H), 7.86 (d, J = 8.6 Hz, 2H), 12.8 (s, 1H). | (ESI+) 557.1 (MH+) | (−) |
| 55 | (2-methylthiazolopyridine with OBu) | (DMSO-d6) δ 0.92 (t, J = 7.3 Hz, 3H), 0.96-1.13 (m, 4H), 1.36-1.77 (m, 7H), 1.86-1.97 (m, 1H), 2.02-2.27 (m, 3H), 2.78-2.86 (m, 1H), 4.07 (t, J = 7.9 Hz, 1H), 4.27 (t, J = 6.7 Hz, 2H), 4.77-5.01 (m, 2H), 6.87 (d, J = 8.6 Hz, 1H), 7.66 (d, J = 8.6 Hz, 2H), 7.88 (d, J = 7.9 Hz, 2H), 8.00 (d, J = 8.6 Hz, 1H), 12.7 (s, 1H). | (ESI+) 564.2 (MH+) | (−) |

TABLE 13

| No. | Structure (A) | 1H NMR (400 MHz) | MS (m/z) | Sign of Optical Rotation |
|---|---|---|---|---|
| 56 | (2-methylthiazolopyridine with OCH2CO2Et) | (DMSO-d6) δ 0.98-1.13 (m, 4H), 1.17 (t, J = 7.3 Hz, 3H), 1.47-1.81 (m, 3H), 1.88-1.99 (m, 1H), 2.04-2.30 (m, 3H), 2.75-2.83 (m, 1H), 4.09 (t, J = 7.9 Hz, 1H), 4.14 (q, J = 7.3 Hz, 2H), 4.77-4.99 (m, 2H), 4.93 (s, 2H), 6.98 (d, J = 8.6 Hz, 1H), 7.64-7.69 (m, 2H), 7.85-7.89 (m, 2H), 8.04 (d, J = 8.6 Hz, 1H), 12.6 (br, 1H). | (ESI+) 594.2 (MH+) | (−) |
| 57 | (1,2-dimethylbenzimidazole) | (CDCl3) δ 0.96-1.04 (m, 2H), 1.31-1.37 (m, 2H), 1.67-1.90 (m, 3H), 1.97-2.08 (m, 1H), 2.08-2.26 (m, 2H), 2.37-2.48 (m, 2H), 3.64 (s, 3H), 3.84 (t, J = 7.6 Hz, 1H), 4.69-4.92 (m, 2H), 7.18-7.32 (m, 4H), 7.65 (d, J = 8.6 Hz, 2H), 7.83 (d, J = 8.6 Hz, 2H), 11.1 (s, 1H). | (ESI+) 488.2 (MH+) | (−) |
| 58 | (3-methylisoxazolopyridine) | (CDCl3) δ 1.04 (ddd, J = 14.1, 6.1, 1.8 Hz, 1H), 1.33-1.38 (m, 2H), 1.70-1.91 (m, 3H), 2.00-2.28 (m, 3H), 2.40-2.49 (m, 2H), 3.91 (t, J = 7.3 Hz, 1H), 4.72-4.93 (m, 2H), 7.40 (dd, J = 8.0, 4.9 Hz, 1H), 7.64 (d, J = 8.0 Hz, 2H), 7.89 (d, J = 8.6 Hz, 2H), 8.66 (dd, J = 4.9, 1.8 Hz, 1H), 8.84 (d, J = 7.3 Hz, 1), 9.34 (br, 1H). | (ESI+) 476.2 (MH+) | (−) |
| 59 | (2-methylthiazole with dioxane) | (DMSO-d6) δ 0.94-1.11 (m, 4H), 1.30 (s, 3H), 1.38 (s, 3H), 1.41-1.15 (m, 3H), 1.75-1.89 (m, 3H), 1.98-2.24 (m, 3H), 2.74-2.85 (m, 1H), 2.97-3.09 (m, 1H), 3.83-4.02 (m, 5H), 4.73-5.01 (m, 2H), 6.96 (s, 1H), 7.61 (d, J = 8.6 Hz, 2H), 7.84 (d, J = 8.6 Hz, 1H), 12.5 (s, 1H). | (ESI+) 555.2 (MH+) | (−) |

TABLE 13-continued

| No. | Structure (A) | 1H NMR (400 MHz) | MS (m/z) | Sign of Optical Rotation |
|---|---|---|---|---|
| 60 | 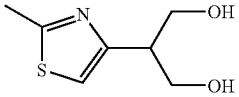 | (DMSO-d6) δ 0.91-1.11 (m, 4H), 1.40-1.75 (m, 3H), 1.75-1.90 (m, 1H), 1.98-2.27 (m, 3H), 2.74-2.88 (m, 2H), 3.50-3.67 (m, 4H), 3.99 (d, J = 7.3 Hz, 1H), 4.40 (dd, J = 5.5, 9.8 Hz, 2H), 4.75-4.99 (m, 2H), 6.18 (s, 1H), 7.62 (d, J = 8.6 Hz, 2H), 7.84 (d, J = 8.6 Hz, 1H), 12.4 (s, 1H). | (ESI+) 515.1 (MH+) | (−) |

TABLE 14

| No. | Structure (A) | 1H NMR (400 MHz) | MS (m/z) | Sign of Optical Rotation |
|---|---|---|---|---|
| 61 | 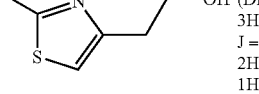 | (DMSO-d6) δ 0.95-1.12 (m, 4H), 1.42-1.75 (m, 3H), 1.79-1.90 (m, 1H), 2.00-2.27 (m, 3H), 2.71 (t, J = 6.7 Hz, 2H), 2.77-2.86 (m, 1H), 3.60-3.67 (m, 2H), 3.99 (t, J = 7.9 Hz, 1H), 4.58 (t, J = 5.5 Hz, 1H), 4.76-5.00 (m, 2H), 6.79 (s, 1H), 7.63 (d, J = 8.6 Hz, 2H), 7.86 (d, J = 8.6 Hz, 2H), 12.4 (br, 1H). | (ESI+) 485.1 (MH+) | (−) |
| 62 | 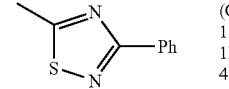 | (CDCl3) δ 1.02-1.13 (m, 2H), 1.33-1.45 (m, 2H), 1.50-1.81 (m, 3H), 1.91-2.11 (m, 3H), 2.29-2.40 (m, 1H), 2.42-2.52 (m, 1H), 3.62 (t, J = 7.6 Hz, 1H), 4.65-4.92 (m, 2H), 7.29 (d, J = 8.6 Hz, 2H), 7.48 (t, J = 3.3 Hz, 3H), 7.84 (d, J = 8.6 Hz, 2H), 8.16-8.23 (m, 2H), 9.98 (s, 1H). | (ESI+) 518.1 (MH+) | (+) |
| 63 | 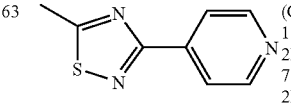 | (CDCl3) δ 0.99-1.09 (m, 2H), 1.32-1.41 (m, 2H), 1.67-1.95 (m, 3H), 2.06-2.25 (m, 3H), 2.25-2.55 (m, 2H), 3.92 (t, J = 7.6 Hz, 1H), 4.71-4.95 (m, 2H), 7.56 (d, J = 8.6 Hz, 2H), 7.91 (dd, J = 8.6, 2.4 Hz, 2H), 8.10 (d, J = 6.1 Hz, 2H), 8.85 (d, J = 8.6 Hz, 2H), 10.7 (s, 1H). | (ESI+) 519.1 (MH+) | (+ (MeOH) |
| 64 | 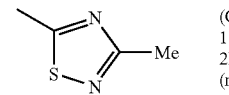 | (CDCl3) δ 1.01-1.14 (m, 2H), 1.32-1.45 (m, 2H), 1.55-1.90 (m, 3H), 2.00-2.22 (m, 3H), 2.38-2.54 (m, 2H), 2.51 (s, 3H), 3.78 (t, J = 7.9 Hz, 1H), 4.69-4.94 (m, 2H), 7.47 (dd, J = 8.6, 1.2 Hz, 2H), 7.89 (dd, J = 8.6, 1.8 Hz, 2H), 9.24-9.44 (m, 1H). | (ESI+) 456.1 (MH+) | (−) |
| 65 | 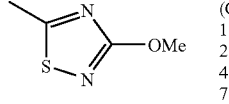 | (CDCl3) δ 1.02 (ddd, J = 14.0, 6.1, 2.4 Hz, 2H), 1.32 (td, J = 6.7, 4.9 Hz, 2H), 1.68-1.92 (m, 3H), 2.00-2.22 (m, 3H), 2.36-2.52 (m, 2H), 4.17 (s, 3H), 4.37 (dd, J = 8.6, 6.7 Hz, 2H), 4.72-4.93 (m, 2H), 7.52 (d, J = 8.6 Hz, 2H), 7.83 (d, J = 8.6 Hz, 2H), 12.4 (s, 1H). | (ESI+) 472.1 (MH+) | (−) (MeOH) |

TABLE 15

| No. | Structure (A) | 1H NMR (400 MHz) | MS (m/z) | Sign of Optical Rotation |
|---|---|---|---|---|
| 66 | 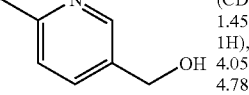 | (CDCl3) δ 0.97-1.04 (m, 2H), 1.06-1.12 (m, 2H), 1.45-1.67 (m, 3H), 1.68-1.77 (m, 1H), 1.77-1.86 (m, 1H), 2.03-2.23 (m, 3H), 2.11-2.84 (m, 1H), 4.05-4.11 (m, 1H), 4.44 (d, J = 5.5 Hz, 2H), 4.78-5.01 (m, 2H), 5.21 (t, J = 5.5 Hz, 1H), 7.64-7.70 (m, 3H), 7.85 (d, J = 8.6 Hz, 2H), 8.01 (d, J = 8.6 Hz, 1H), 8.23 (d, J = 1.8 Hz, 1H), 10.8 (s, 1H). | (ESI+) 485.2 (MH+) | (−) (DMF) |

Reference Example 1

(1α,3α,4α)-3,4-Difluorocyclopentylmethyl iodide

First Step

[(1α,3β,4β)-3,4-Dihydroxycyclopentyl]methyl benzoate

[Chemical formula 13]

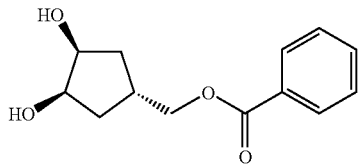

N-methylmorpholine N-oxide (50% aqueous solution, 22.0 mL) and osmium tetraoxide (2.5% t-butanol solution, 1.90 mL) were dissolved in acetone (190 mL), and a solution of (3-cyclopenten-1-yl)methyl benzoate (WO 93/18009, Japanese Translation of PCT International Application No. Hei 7-506816) (20.2 g) in acetone (125 mL) was added dropwise thereto over 105 minutes while stirring. The mixture was then stirred for a further 15 hours at room temperature. To this reaction mixture chloroform (310 mL) and water (190 mL) were added, and the organic layer was separated. The separated organic layer was washed with 1 mol/L hydrochloric acid (2×90 mL), water (90 mL), and a saturated aqueous sodium bicarbonate solution (60 mL) in that order, dried over anhydrous sodium sulfate, and then concentrated under reduced pressure. Toluene (120 mL) was added to the resulting residue. The precipitated crystals were collected by filtration to obtain [(1α,3β,4β)-3,4-dihydroxycyclopentyl]methyl benzoate (16.9 g).

$^1$H NMR (CDCl$_3$) δ 1.71-1.78 (m, 2H), 1.95-2.02 (m, 2H), 2.27 (br, 2H), 2.75-2.87 (m, 1H), 4.19-4.23 (m, 4H), 7.43-7.47 (m, 2H), 7.55-7.59 (m, 1H), 8.01-8.04 (m, 2H).

The filtrate was concentrated under reduced pressure to obtain a mixture of [(1α,3β,4β)-3,4-dihydroxycyclopentyl]methyl benzoate and [(1β,3β,4β)-3,4-dihydroxycyclopentyl]methyl benzoate (4.23 g, based on the $^1$H NMR integral ratio, a 1:2 mixture).

$^1$H NMR (CDCl$_3$) δ 1.58-1.65 (m, 1.3H), 1.71-1.78 (m, 0.7H), 1.96-2.17 (m, 2H), 2.75-2.85 (m, 1H), 4.09-4.32 (m, 4H), 7.42-7.46 (m, 2H), 7.54-7.59 (m, 1H), 8.01-8.06 (m, 2H).

Second Step (3aα,5α,6aα)-(Tetrahydro-4H-cyclopenta-1,3,2-dioxathiol-5-yl)methyl benzoate S,S-dioxide

[Chemical formula 14]

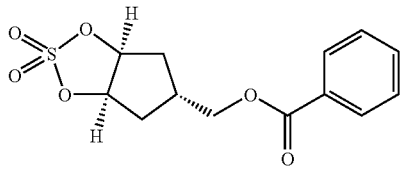

[(1α,3β,4β)-3,4-Dihydroxycyclopentyl]methyl benzoate (5.00 g) was suspended in carbon tetrachloride (75 mL). Thionyl chloride (1.90 mL) was added to the resultant suspension, and then the mixture was heated to reflux for 1.5 hours while stirring. Thionyl chloride (0.50 mL) was further added to the reaction mixture, and then the mixture was heated to reflux for another 1 hour while stirring. The reaction mixture was concentrated under reduced pressure, and to the resulting residue toluene (25 mL) was added. The mixture was again concentrated under reduced pressure, then dried under reduced pressure to obtain (3aα,5α,6aα)-(tetrahydro-4H-cyclopenta-1,3,2-dioxathiol-5-yl) methyl benzoate S-oxide (6.09 g). The obtained (3aα,5α,6aα)-(tetrahydro-4H-cyclopenta-1,3,2-dioxathiol-5-ylmethyl benzoate S-oxide (4.27 g), acetonitrile (30 mL), and carbon tetrachloride (30 mL) were mixed. To the resulting mixture, sodium periodate (6.46 g), ruthenium chloride hydrate (31.3 mg), and then water (30 mL) were added. The reaction mixture was stirred for 30 minutes at room temperature, to which dichloromethane (50 mL) was added. Insoluble matter was filtered off. The organic layer of the filtrate was collected, and the aqueous layer of the filtrate was extracted with dichloromethane (50 mL). The organic layer and the dichloromethane extract were combined, and the resulting mixture was washed with a 1 mol/L aqueous sodium thiosulfate solution (2×40 mL) and then with water (2×40 mL). The mixture was dried over anhydrous sodium sulfate, and then concentrated under reduced pressure. The resulting residue was dried under reduced pressure to obtain (3aα,5α,6aα)-(tetrahydro-4H-cyclopenta-1,3,2-dioxathiol-5-yl)methyl benzoate S,S-dioxide (4.35 g).

MS (CI$^+$) m/z: 299 (MH$^+$).

HRMS (CI$^+$) for C$_{13}$H$_{15}$O$_6$S (MH$^+$): calcd., 299.0589; found, 299.0593.

Third Step

[(1α,3α,4β)-3-Fluoro-4-hydroxycyclopentyl]methyl benzoate

[Chemical formula 15]

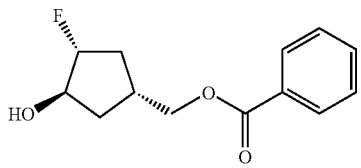

Tetrabutylammoniumfluoride hydrate (571 mg) was dissolved in dehydrated acetonitrile (5 mL), and the resulting mixture was concentrated under reduced pressure. The same operation was repeated twice, and the resulting residue was dried for 45 minutes under reduced pressure at 40° C. This residue was dissolved in dehydrated acetonitrile (5 mL), and to the resulting mixture (3aα,5α,6aα)-(tetrahydro-4H-cyclopenta-1,3,2-dioxathiol-5-yl) methyl benzoate S,S-dioxide (500 mg) was added. The mixture was heated to reflux for 45 minutes while stirring, and the resultant reaction mixture was then concentrated under reduced pressure. The residue was dissolved in ethanol (5 mL), and to the resulting mixture sulfuric acid (0.15 mL) was added. The mixture was heated to reflux for 10 minutes while stirring, and the resultant reaction mixture was then concentrated under reduced pressure. The residue was dissolved in ethyl acetate (40 mL), and the resulting mixture was washed with a saturated aqueous sodium bicarbonate solution (5 mL) and then with saturated brine (5 mL). The resulting mixture was dried over anhydrous sodium sulfate, then concentrated under reduced pressure. The resulting residue was purified by a silica gel column (eluant; hexane:ethyl acetate=1:1) to obtain [(1α,3α,4α)-3-fluoro-4-hydroxycyclopentyl]methyl benzoate (342 mg).

MS (EI) m/z: 238 (M$^+$)

HRMS (EI) for $C_{13}H_{15}FO_3$ (M$^+$) calcd., 238.1005; found, 238.1046.

Fourth Step

[(1α,3α,4α)-3,4-Difluorocyclopentyl]methyl benzoate

[Chemical formula 16]

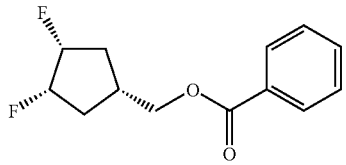

[(1α,3α,4β)-3-Fluoro-4-hydroxycyclopentyl]methyl benzoate (326 mg) was dissolved in dehydrated tetrahydrofuran (5 mL), and to the resulting mixture a solution of bis(2-methoxyethyl)aminosulfur trifluoride (455 mg) in dehydrated tetrahydrofuran (2 mL) was added. The resulting mixture was heated to reflux for 1.5 hours while stirring. This reaction mixture was poured into a saturated aqueous sodium bicarbonate solution (10 mL) and then extracted with ethyl acetate (2×30 mL). The ethyl acetate extracts were combined, the resulting mixture was washed with saturated brine (2×10 mL), dried over anhydrous sodium sulfate, and then concentrated under reduced pressure. The resulting residue was purified by a silica gel column (eluant; hexane:ethyl acetate=4:1) to obtain [(1α,3α,4α)-3,4-difluorocyclopentyl]methyl benzoate (233 mg).

MS (CI$^+$) m/z: 241 (MH$^+$).

HRMS (CI$^+$) for $C_{13}H_{15}F_2O_2$ (MH$^+$): calcd., 241.1040; found, 241.1043.

Fifth Step

[(1α,3α,4α)-3,4-Difluorocyclopentyl]methanol

[Chemical formula 17]

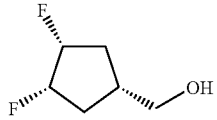

[(1α,3α,4α)-3,4-Difluorocyclopentyl]methyl benzoate (221 mg) was dissolved in ethanol (3 mL), and to the resulting mixture a solution of potassium carbonate (191 mg) in water (1 mL) was added. The mixture was then heated to reflux for 4 hours while stirring. The reaction mixture was concentrated under reduced pressure, and the resulting residue was purified by a silica gel column (eluant; hexane:ethyl acetate=1:2) to obtain [(1α,3α,4α)-3,4-difluorocyclopentyl]methanol (123 mg).

MS (CI$^+$) m/z: 137 (MH$^+$).

HRMS (CI$^+$) for $C_6H_{11}F_2O$ (MH$^+$): calcd., 137.0778; found, 137.0801.

Sixth Step (1α,3α,4α)-3,4-Difluorocyclopentylmethyl iodide

[Chemical formula 18]

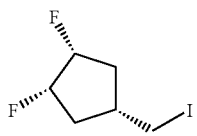

Iodine (120 mg) was added under ice-cooling to a solution of imidazole (64.5 mg) and triphenylphosphine (124 mg) in dichloromethane (2.0 mL), and the resulting mixture was stirred for 30 minutes at room temperature. Then, to the mixture a solution of [(1α,3α,4α)-3,4-difluorocyclopentyl]methanol (43.0 mg) in dichloromethane (0.5 mL) was added, and the resulting mixture was stirred for 4 hours at room temperature. Insoluble matter was then was filtered off, and the filtrate was concentrated. The resulting residue was purified by silica gel column chromatography to obtain (1α,3α, 4α)-3,4-difluorocyclopentylmethyl iodide (28.0 mg).

MS (EI) m/z: 246 (M$^+$).

HRMS (EI) for $C_6H_9F_2I$ (M$^+$): calcd., 245.9717; found, 245.9741.

Seventh Step (1α,3α,4α)-(3,4-Difluorocyclopentyl)methylphosphonium iodide

[Chemical formula 19]

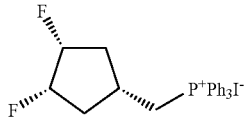

(1α,3α,4α)-3,4-Difluorocyclopentylmethyl iodide (9.84 g), triphenylphosphine (12.6 g), and acetonitrile (3 mL) were mixed, and the resulting mixture was stirred for 4 hours at 90 to 95° C. Acetonitrile (2 mL) was added to this reaction mixture, and then the mixture was stirred for another 20 hours at 90 to 95° C. The reaction mixture was cooled, then to which diethyl ether (50 mL) was added. The precipitated crystals were collected by filtration. The collected crystals were suspended in diethyl ether (50 mL), and then collected by filtration. The crystals were washed with a suitable amount of diethyl ether, then dried under reduced pressure to obtain the title compound (20 g). The title compound is useful in producing the compound according to the present invention with a good yield. $^1$H NMR (400 MHz, CDCl$_3$) δ 1.72-1.85 (m, 2H), 2.17-2.29 (m, 2H), 2.69-2.82 (m, 1H), 3.86 (dd, J=7.3, 2.4 Hz, 1H), 3.89 (dd, J=7.3, 2.4 Hz, 1H), 4.74-4.92 (m, 2H), 7.31-7.90 (m, 15H).

Reference Example 2

(1β,3α,4α)-3,4-Difluorocyclopentylmethyl iodide

First Step

(3aα,5β,6aα)-(Tetrahydro-4H-cyclopenta-1,3,2-dioxathiol-5-yl)methyl benzoate S,S-dioxide A mixture (4.23 g) of the [(1α,3β,4β)-3,4-dihydroxycyclopentyl]methyl benzoate and [(1β,3β,4β)-3,4-dihydroxycyclopentyl]methyl benzoate obtained in the first step of Reference Example 1 and carbon tetrachloride (75 mL) were mixed. Thionyl chloride (2.00 mL) was added to the resulting mixture, and then the mixture was heated to reflux for 30 minutes while stirring. The reaction mixture was concentrated under reduced pressure, and toluene (75 mL) was added to the resulting residue. This mixture was concentrated under reduced pressure, and the resulting residue was dried under reduced pressure. This residue was mixed with acetonitrile (35 mL g) and carbon tetrachloride (35 mL), and sodium periodate (7.66 g), ruthenium chloride hydrate (37.1 mg), and then water (35 mL) were added to the resulting mixture. The reaction mixture was stirred for 30 minutes at room temperature. Dichloromethane (60 mL) was then added to the reaction mixture. Insoluble matter was filtered off, and then, the organic layer of the filtrate was collected. The aqueous layer of the filtrate was extracted with dichloromethane (60 mL). The organic layer and the dichloromethane extract were combined, and the resulting mixture was washed with a 1 mol/L aqueous sodium thiosulfate solution (2×50 mL) and then with water (2×50 mL). The mixture was dried over anhydrous sodium sulfate, and then concentrated under reduced pressure. The resulting residue was purified by a silica gel column (eluant; hexane:ethyl acetate=1:1) to obtain (3aα,5β,6aα)-(tetrahydro-4H-cyclopenta-1,3,2-dioxathiol-5-yl)methyl benzoate S,S-dioxide (2.43 g) and (3aα,5α,6aα)-(tetrahydro-4H-cyclopenta-1,3,2-dioxathiol-5-yl)methyl benzoate S,S-dioxide (1.33 g).

MS (EI) m/z: 298 (M$^+$).
HRMS (EI) for $C_{13}H_{14}O_6S$ (M$^+$): calcd., 298.0511; found, 298.0493.

Second Step

[(1β,3α,4β)-3-Fluoro-4-hydroxycyclopentyl]methyl benzoate

Using (3aα,5β,6aα)-(tetrahydro-4H-cyclopenta-1,3,2-dioxathiol-5-yl)methyl benzoate S,S-dioxide (1.00 g), [(1β,3α4β)-3-fluoro-4-hydroxycyclopentyl]methyl benzoate (660 mg) was obtained by carrying out a reaction in the same manner as in the third step of Reference Example 1.

MS (CI$^+$) m/z: 239 (MH$^+$).
HRMS (CI$^+$) for $C_{13}H_{16}FO_3$ (MH$^+$): calcd., 239.1083; found, 239.1040.

Third Step

[(1β,3α,4α)-3,4-Difluoro-cyclopentyl]methyl benzoate

Using [(1β,3α,4β)-3-fluoro-4-hydroxycyclopentyl]methyl benzoate (644 mg), [(1β,3α,4α)-3,4-difluoro-cyclopentyl]methyl benzoate (365 mg) was obtained by carrying out a reaction in the same manner as in the fourth step of Reference Example 1.

MS (CI$^+$) m/z: 241 (MH$^+$).
HRMS (CI$^+$) for $C_{13}H_{15}F_2O_2$ (MH$^+$): calcd., 241.1040; found, 241.1012.

Fourth Step

[(1β,3α,4α)-3,4-Difluorocyclopentyl]methanol

Using [(1β,3α,4α)-3,4-difluoro-cyclopentyl]methylbenzoate (349 mg), [(1β,3α,4α)-3,4-difluorocyclopentyl]methanol (184 mg) was obtained by carrying out a reaction in the same manner as in the fifth step of Reference Example 1.

MS (CI$^+$) m/z: 137 (MH$^+$).
HRMS (CI$^+$) for $C_6H_{11}F_2O$ (MH$^+$): calcd., 137.0778; found, 137.0754.

Fifth Step

(1β,3α,4α)-3,4-Difluorocyclopentyl iodide

Using [(1β,3α,4α)-3,4-difluorocyclopentyl]methanol (3.46 g), (1β,3α,4α)-3,4-difluorocyclopentyl iodide (4.72 g) was obtained by carrying out a reaction in the same manner as in the sixth step of Reference Example 1.

MS (EI) m/z: 246 (M$^+$).
HRMS (EI) for $C_6H_9F_2I$ (M$^+$): calcd., 245.9717; found, 245.9749.

Reference Example 3

(+)-2-[4-(Cyclopropylsulfonyl)phenyl]-3-[(1α,3α,4α)-3,4-difluorocyclopentyl]-N-(thiazol-2-yl)propionamide

[Chemical formula 20]

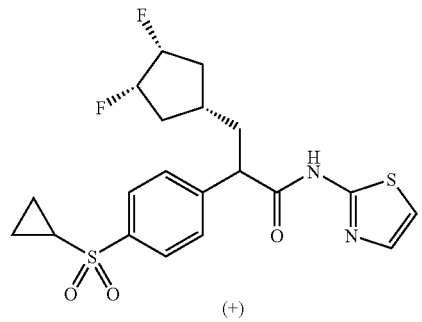

(+)

(+)-2-[4-(Cyclopropylsulfonyl)phenyl]-3-[(1α,3α,4α)-3,4-difluorocyclopentyl]-N-(thiazol-2-yl)propionamide (105 mg) was obtained from (+)-2-[4-(cyclopropylsulfonyl)phenyl]-3-[(1α,3α,4α)-3,4-difluorocyclopentyl]-N-(thiazol-2-yl) propionic acid (300 mg) according to the same method as in Example 5.

MS (ESI$^+$) m/z: 441 (ESI$^+$).
HRMS (ESI$^+$) for $C_{20}H_{23}F_2N_2O_3S_2$ (ESI$^+$): calcd., 441.11181; found, 441.11177.

$^1$H NMR (400 MHz, CDCl$_3$) δ 1.00-1.09 (m, 2H), 1.32-1.38 (m, 2H), 1.64-1.89 (m, 3H), 2.00-2.22 (m, 3H), 2.37-2.50 (m, 2H), 3.72 (t, J=7.6 Hz, 1H), 4.70-4.91 (m, 2H), 7.04

(d, J=3.7 Hz, 1H), 7.46 (d, J=3.7 Hz, 1H), 7.49 (d, J=7.9 Hz, 2H), 7.86 (d, J=7.9 Hz, 2H), 10.1 (brs, 1H).

Reference Example 4

2-(5-Aminopyrazin-2-ylthio)ethanol

[Chemical formula 21]

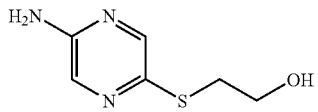

Based on the method described in WO2004/052869, mercaptoethanol (0.93 mL) and tetrakis(triphenylphosphine)palladium (3.39 g) were added to a solution of 1.00 g of 2-amino-5-bromopyrazine (5.75 mmol) in N,N-dimethylformamide (15.1 mL), and the resulting mixture was heated and stirred in a sealed tube for about 3 hours at 120° C. After cooling, the reaction mixture was diluted with water, and then extracted (100 mL×6) with a mixed liquid (methylene chloride:ethanol=5:1). The organic layer was dried over anhydrous sodium sulfate, then filtered, and the solvent was removed by distillation under reduced pressure. The resulting residue was purified by column chromatography (hexane:ethyl acetate=1:1, then ethyl acetate, and then ethyl acetate:methanol=10:1), then recrystallized (chloroform) to obtain 470 mg of the title compound (yield 44%) as yellow needle-like crystals.

MS (EI$^+$) m/z: 171 (M$^+$).
HRMS (EI$^+$) for $C_6H_9N_3OS$ (M$^+$): calcd., 171.0466; found, 171.0451.

Reference Example 5

5-[2-(Methylthio)ethoxy]pyrazine-2-amine

[Chemical formula 22]

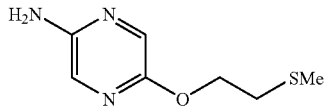

Based on the method described in WO2007/007886, sodium hydride
(50% oily substance) (314 mg) was added to methylthioethanol (7.88 mL) under stirring with ice cooling, and then copper (490 mg) and 2-amino-5-bromopyrazine (1.00 g) were added to the resulting mixture. The reaction mixture was placed in an autoclave, and then heated and stirred for about 5 hours at 160° C. After cooling, to the reaction mixture water (50 mL) and ethyl acetate (50 mL) were added to dilute the mixture. Then, the mixture was turned into a basic solution by adding 25% ammonia water (2 mL). The reaction mixture was filtered with Celite and then separated into an organic layer and an aqueous layer. The aqueous layer was extracted with ethyl acetate (50 mL×2). The organic layers were combined, and was dried over anhydrous sodium sulfate, then filtered, and the solvent was removed by distillation under reduced pressure. The resulting residue was purified by silica gel chromatography (hexane:ethyl acetate=1:1), then by preparative TLC (chloroform:methanol=10:1, followed by NH silica gel, hexane:acetone=3:1), to obtain 59.2 mg of the title compound (yield 6%) as white powdery crystals.

MS (EI$^+$) m/z: 185 (M$^+$).
HRMS (EI$^+$) for $C_7H_{11}N_3OS$ (M$^+$): calcd., 185.0623; found, 185.0613.

Reference Example 6

5-(2-Ethoxyethoxy)pyrazine-2-amine

[Chemical formula 23]

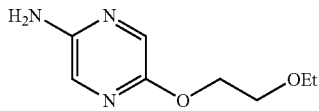

1.50 g of the title compound (yield 41%) was obtained as yellow crystals from 2-amino-5-bromopyrazine (3.48 g) and ethoxyethanol (36.0 g) according to the method of Reference Example 5.

MS (EI$^+$) m/z: 183 (M$^+$).
HRMS (EI$^+$) for $C_8H_{13}N_3O_2$ (M$^+$): calcd., 183.1008; found, 183.0996.

Reference Example 7

5-(3-Methoxypropoxy)pyrazine-2-amine

[Chemical formula 24]

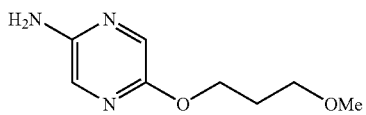

644 mg of the title compound (yield 18%) was obtained as yellow crystals from 2-amino-5-bromopyrazine (3.48 g) and methoxypropanol (18.0 g) according to the method of Reference Example 5.

MS (EI$^+$) m/z: 183 (M$^+$).
HRMS (EI$^+$) for $C_8H_{13}N_3O_2$ (M$^+$): calcd., 183.1008; found, 183.1011.

Reference Example 8

(−)-2-[4-(Cyclopropylsulfonyl)phenyl]-3-[(1β,3α, 4α)-3,4-difluorocyclopentyl]-N-(thiazol-2-yl)propionamide and (+)-2-[4-(cyclopropylsulfonyl)phenyl]-3-[(1β,3α,4α)-3,4-difluorocyclopentyl]-N-(thiazol-2-yl)propionamide (1β,3α,4α)-(3,4-Difluorocyclopentyl)methylphosphonium iodide was produced in the same manner as in the seventh step of Reference Example 1 from the (1β,3α,4α)-3,4-difluorocyclopentylmethyl iodide obtained in the fifth step of Reference Example 2. The title compounds were then obtained in the same manner as in Examples 2, 3, and 4 and in Example 5.

Test Example 1

Measurement of GK Activity

GK activity was examined not by directly measuring glucose 6-phosphate produced by an enzyme reaction, but by measuring the amount of NADH produced by a conjunction reaction catalyzed by glucose-6-dehydrogenase.

(Preparation of Recombinant Gk)

Human Hepatic and Pancreatic GK Cloning and Acquisition of Recombinant Protein

Based on the human hepatic GK sequence accession number: NM_033507 and human pancreatic GK sequence accession number: NM_000162, which are registered in the GeneBank, PCR cloning was carried out by Pyrobest DNA Polymerase (manufactured by Takara Bio Inc.) with human liver cDNA (manufactured by Clontech) and human pancreatic cDNA (manufactured by Clontech) as respective templates. Furthermore, the cloned genes were expressed in the soluble fraction in *E. coli* as a His-tagged fusion protein that was (His)-6 tagged at the C terminal side. The bacterium was subjected to ultrasonic disintegration, then subjected to centrifugal separation, and the supernatant was recovered. The collected supernatant was purified by metal chelate affinity chromatography.

After the purification, the resulting enzyme was stored at −80° C. in 12.5 mM HEPES (pH 7.3), 75 mM KCl, 0.5 mM $MgCl_2$, 0.5 mM DTT, 2.5 mM glucose, and 50% glycerol.

(Measurement of GK Activity)

An assay was carried out at 25° C. using a 96 well half area flat bottom plate manufactured by Costar. An incubation mixture was prepared so as to ultimately include 25 mM HEPES buffer solution (pH 7.1) (manufactured by Invitrogen), 25 mM KCl (manufactured by Wako Pure Chemical Industries Ltd.), 2 mM $MgCl_2$ (manufactured by Wako Pure Chemical Industries Ltd.), 5 mM D-glucose (manufactured by Wako Pure Chemical Industries Ltd.), 1 mM ATP (manufactured by Roche), 1 mM NAD (manufactured by Sigma), 1 mM dithiothreitol (manufactured by Wako Pure Chemical Industries Ltd.), 5 unit/mL G6PDH (manufactured by Sigma), and a 0.1% BSA (manufactured by Sigma), and a test compound or 5% DMSO and GK.

The compound to be tested was dissolved in DMSO in advance, and 2 µL of the resulting mixture was added to 20 µL of a solution including a HEPES buffer solution (pH 7.1), KCl, $MgCl_2$, D-glucose, ATP, NAD, and dithiothreitol. Next, 18 µL of a solution including G6PDH, BSA, and recombinant GK was added to the mixture in order to initiate the reaction. GK was added into the reaction mixture so that the increase in absorbance per minute in the presence of 5% DMSO was between 0.002 and 0.003. Once the reaction started, the increase in absorbance at 340 nm was measured for 15 minutes using a SPECTRAmax 190 microplate spectrophotometer (manufactured by Molecular Devices). The activity was evaluated using the amount of increase for the first 10 minutes.

A human liver GK-activating effect of 200% or more at 10 µM was found for Compounds 1 to 15, 17 to 37, 42 to 46, 55, and 56 of the present invention, when compared with the wells that did not contain such compound.

Test Example 2

Hypoglycemic Activity Test

Using ICR mice (male, 7 to 9 weeks, Charles River Laboratories Japan Inc.) the effects of each of the tested compounds on blood glucose levels were measured. Each compound was dissolved in a mixture of 60/40 of Gelucire 44/14 (trade name, manufactured by Gatefosse) and PEG 400, and the resulting mixture was orally administered (30 mg/kg, 10 mL/kg) to the mice, which had not been fed for two hours. Blood was collected by a blood collection tube coated with dipotassium ethylenediamine tetraacetate from the tail vein before administration (pre-value) and at points 0.5, 2, and 4 hours after administration. The collected blood was separated by centrifugation (4° C., 3,600×g, 3 minutes), to obtain blood plasma samples.

Each sample was diluted 5-fold with physiological saline, and the blood glucose level was measured using glucose CII-test Wako (trade name, manufactured by Wako Pure Chemical Industries Ltd.). 10 µL each of one of the samples, physiological saline, and 100 mg/dL of glucose standard solution (200 mg/dL of glucose standard solution diluted two-fold with physiological saline) were placed in each well of a 96 well flat bottom plate. Then, 150 µL per well of a developing solution was added, and the color was developed by standing for 5 minutes at 37° C. Measurement was carried out at OD 505 nm using an EnVision 2103 Multilabel Reader (trade name, manufactured by PerkinElmer). The decrease in Σ glucose from the decrease in glucose of each collected point with respect to the pre-value (average of the decrease in glucose of each collected point with respect to the pre-value) was calculated.

A decrease of 35% or more in Σ glucose was found for Compounds 1 to 6, 8, 13, 15, 18, 21 to 23, 28, 31, 34, 35, 51, 64, and 65 of the present invention.

None of the (+)-2-[4-(cyclopropylsulfonyl)phenyl]-3-[(1α,3α,4α)-3,4-difluorocyclopentyl]-N-(thiazol-2-yl) propionamide produced in Reference Example 3, the (−)-2-[4-(cyclopropylsulfonyl)phenyl]-3-[(1β,3α,4α)-3,4-difluorocyclopentyl]-N-(thiazol-2-yl) propionamide produced in Reference Example 8, or the (+)-2-[4-(cyclopropylsulfonyl)phenyl]-3-[(1β,3α,4α)-3,4-difluorocyclopentyl]-N-(thiazol-2-yl) propionamide produced in Reference Example 8 showed a decrease in Σ glucose which exceeded 20%.

INDUSTRIAL APPLICABILITY

The glucokinase activator of the present invention has an excellent GK-activating effect or hypoglycemic effect, and few side effects (for example, prolonged QT interval, hypoglycemia symptoms etc.). Therefore, the glucokinase activator of the present invention is useful as a pharmaceutical for the treatment or prevention of diabetes, obesity and the like.

The invention claimed is:

1. A compound represented by the general formula (I), or a pharmaceutically acceptable salt thereof:

[Chemical formula 1]

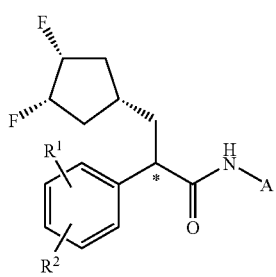

(1)

(wherein, the carbon atom marked with an * is in the R-configuration, $R^1$ represents a hydrogen atom, a halogen atom, an amino group, a hydroxyl group, a hydroxyamino group, a nitro group, a cyano group, a sulfamoyl group, a $C_1$-$C_6$ alkyl group, or a $C_1$-$C_6$ alkoxy group, $R^2$ represents a $C_3$-$C_6$ cycloalkylsulfanyl group, a $C_3$-$C_6$ cycloalkylsulfinyl group, or a $C_3$-$C_6$ cycloalkylsulfonyl group, and A represents a substituted or unsubstituted heteroaryl group).

2. The compound according to claim 1, or a pharmaceutically acceptable salt thereof, wherein $R^1$ is a hydrogen atom and $R^2$ is a $C_3$-$C_6$ cycloalkylsulfonyl group.

3. The compound according to claim 1, or a pharmaceutically acceptable salt thereof, wherein $R^1$ is a hydrogen atom and $R^2$ is a cyclopropylsulfonyl group.

4. The compound according to claim 1, represented by the general formula (1a), or a pharmaceutically acceptable salt thereof:

[Chemical formula 2]

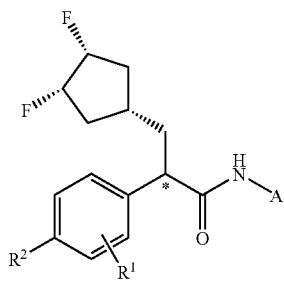

(1a)

(wherein the *, $R^1$, $R^2$, and A are as defined in claim 1).

5. The compound according to claim 1, represented by the general formula (1b), or a pharmaceutically acceptable salt thereof:

[Chemical formula 3]

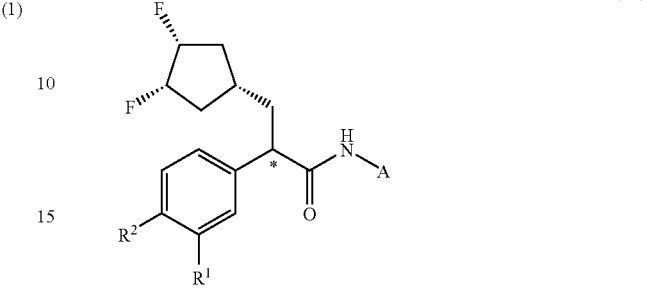

(1b)

(wherein the *, $R^1$, $R^2$, and A are as defined in claim 1).

6. The compound according to claim 1, or a pharmaceutically acceptable salt thereof, wherein A is a heteroaryl group that is unsubstituted or monosubstituted with a halogen atom, a $C_1$-$C_6$ alkyl group, a $C_1$-$C_6$ alkoxy group, a nitro group, a cyano group, or a group represented by the formula,

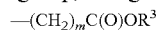

(wherein $R^3$ represents a hydrogen atom or a $C_1$-$C_6$ alkyl group and m is an integer of 0 to 2).

7. The compound according to claim 1, or a pharmaceutically acceptable salt thereof, wherein A is a heteroaryl group unsubstituted or monosubstituted with a halogen atom or a $C_1$-$C_6$ alkyl group.

8. The compound according to claim 6, or a pharmaceutically acceptable salt thereof, wherein A is an unsubstituted or monosubstituted 5- or 6-membered aromatic heterocyclic ring that contains 1 to 3 heteroatoms selected from a sulfur atom, an oxygen atom, and a nitrogen atom, with one of those heteroatoms being a nitrogen atom adjacent to a ring-linking atom.

9. The compound according to claim 6, or a pharmaceutically acceptable salt thereof, wherein A is an unsubstituted or monosubstituted fused heterocyclic ring having a 5- or 6-membered aromatic heterocyclic ring that contains 1 to 3 heteroatoms selected from a sulfur atom, an oxygen atom, and a nitrogen atom, with one of those heteroatoms being a nitrogen atom adjacent to a ring-linking atom.

10. The compound according to claim 6, or a pharmaceutically acceptable salt thereof, wherein A is an unsubstituted or substituted aromatic heterocyclic ring selected from the following:

[Chemical formula 4]

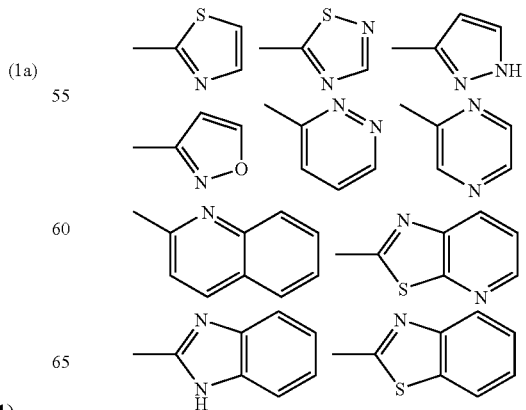

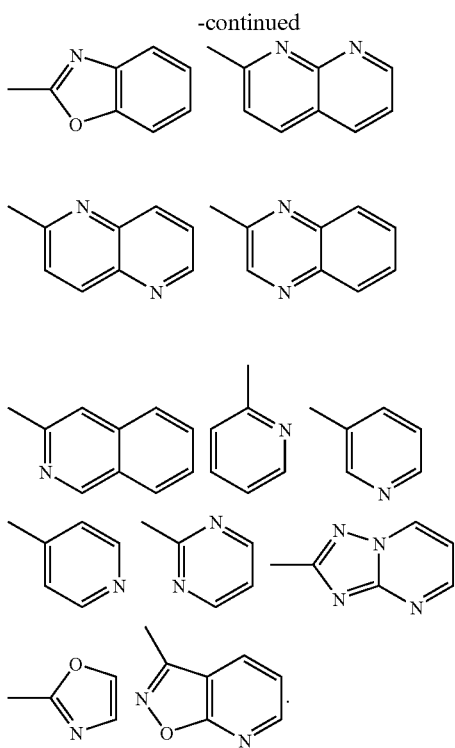

11. (−)-2-[4-(Cyclopropylsulfonyl)phenyl]-3-[(1α,3α,4α)-3,4-difluorocyclopentyl]-N-(thiazol-2-yl)propionamide or a pharmaceutically acceptable salt thereof.

12. (−)-2-[4-(Cyclopropylsulfonyl)phenyl]-3-[(1α,3α,4α)-3,4-difluorocyclopentyl]-N-(5-fluorothiazol-2-yl)propionamide or a pharmaceutically acceptable salt thereof.

13. (−)-2-[4-(Cyclopropylsulfonyl)phenyl]-3-[(1α,3α,4α)-3,4-difluorocyclopentyl]-N-(pyrazin-2-yl)propionamide or a pharmaceutically acceptable salt thereof.

14. (−)-2-[4-(Cyclopropylsulfonyl)phenyl]-3-[(1α,3α,4α)-3,4-difluorocyclopentyl]-N-(5-fluoropyridin-2-yl)propionamide or a pharmaceutically acceptable salt thereof.

15. A method of treating diabetes, comprising administering the compound according to claim 1, or a pharmaceutically acceptable salt thereof.

16. A pharmaceutical composition comprising the compound according to claim 1, or a pharmaceutically acceptable salt thereof, and a pharmaceutically acceptable carrier.

17. A compound represented by the general formula (3):

[Chemical formula 5]

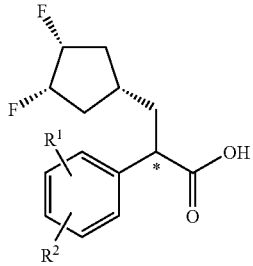

(3)

(wherein, the carbon atom marked with an * is in the R-configuration, $R^1$ represents a hydrogen atom, a halogen atom, an amino group, a hydroxyl group, a hydroxyamino group, a nitro group, a cyano group, a sulfamoyl group, a $C_1$-$C_6$ alkyl group, or a $C_1$-$C_6$ alkoxy group, and $R^2$ represents a $C_3$-$C_6$ cycloalkylsulfanyl group, a $C_3$-$C_6$ cycloalkylsulfinyl group, or a $C_3$-$C_6$ cycloalkylsulfonyl group).

18. The compound according to claim 17, wherein $R^1$ is a hydrogen atom and $R^2$ is a $C_3$-$C_6$ cyclopropylsulfonyl group.

19. A method of treating diabetes, comprising administering the compound according to claim 11, or a pharmaceutically acceptable salt thereof.

20. A method of treating diabetes, comprising administering the compound according to claim 12, or a pharmaceutically acceptable salt thereof.

21. A method of treating diabetes, comprising administering the compound according to claim 13, or a pharmaceutically acceptable salt thereof.

22. A method of treating diabetes, comprising administering the compound according to claim 14, or a pharmaceutically acceptable salt thereof.

23. A pharmaceutical composition comprising the compound according to claim 11, or a pharmaceutically acceptable salt thereof, and a pharmaceutically acceptable carrier.

24. A pharmaceutical composition comprising the compound according to claim 12, or a pharmaceutically acceptable salt thereof, and a pharmaceutically acceptable carrier.

25. A pharmaceutical composition comprising the compound according to claim 13, or a pharmaceutically acceptable salt thereof, and a pharmaceutically acceptable carrier.

26. A pharmaceutical composition comprising the compound according to claim 14, or a pharmaceutically acceptable salt thereof, and a pharmaceutically acceptable carrier.

* * * * *